US012742190B2

(12) United States Patent
Pick

(10) Patent No.: US 12,742,190 B2
(45) Date of Patent: Sep. 22, 2026

(54) PRODUCTION OF FRUCTOSE FROM OLIGO-/ AND/OR POLYSACCHARIDES

(71) Applicant: Archer-Daniels-Midland Company, Decatur, IL (US)

(72) Inventor: André Pick, Bebra-Breitenbach (DE)

(73) Assignee: Archer-Daniels-Midland Company

( * ) Notice: Subject to any disclaimer, the term of this patent is extended or adjusted under 35 U.S.C. 154(b) by 519 days.

(21) Appl. No.: 17/787,149

(22) PCT Filed: Dec. 21, 2020

(86) PCT No.: PCT/EP2020/087480
§ 371 (c)(1), (2) Date: Jun. 17, 2022

(87) PCT Pub. No.: WO2021/123436
PCT Pub. Date: Jun. 24, 2021

(65) Prior Publication Data

US 2023/0038016 A1 Feb. 9, 2023

(30) Foreign Application Priority Data

Dec. 20, 2019 (EP) .................................... 19218550

(51) Int. Cl.
*C12P 19/02* (2006.01)
*C12N 9/10* (2006.01)
*C12N 9/16* (2006.01)
*C12N 9/24* (2006.01)
*C12N 9/90* (2006.01)

(52) U.S. Cl.
CPC ............ *C12P 19/02* (2013.01); *C12N 9/1051* (2013.01); *C12N 9/16* (2013.01); *C12N 9/2402* (2013.01); *C12N 9/90* (2013.01); *C12Y 204/01* (2013.01); *C12Y 301/03* (2013.01); *C12Y 302/01041* (2013.01); *C12Y 503/01* (2013.01); *C12Y 504/02* (2013.01)

(58) Field of Classification Search
CPC ........... C12P 19/02; C12P 19/18; C12P 19/04; C12N 9/1051; C12N 9/16; C12N 9/2402; C12N 9/90; C12N 9/2457; C12Y 204/01; C12Y 301/03; C12Y 302/01041; C12Y 503/01; C12Y 504/02; C12Y 204/01001; C12Y 204/01025; C12Y 301/03023; C12Y 503/01009; C12Y 504/02002; C12Y 504/02005
See application file for complete search history.

(56) References Cited

U.S. PATENT DOCUMENTS

2002/0007081 A1 1/2002 Schelhaas et al.

FOREIGN PATENT DOCUMENTS

| | | | |
|---|---|---|---|
| DE | 10 2017 002252 | A1 | 9/2018 |
| JP | 2002053540 | A | 2/2002 |
| JP | 2005087149 | A | 4/2005 |
| JP | 2019-085303 | A | 6/2019 |
| KR | 10-2019-0128681 | A | 11/2019 |
| WO | 2018169957 | A1 | 9/2018 |

OTHER PUBLICATIONS

New England Biolabs. (2025). Neb.com. https://www.neb.com/en-us/protocols/0001/01/01/protocol-ii-1-m-tris-hcl-buffer-stock-solution-1-liter (Year: 2025).*

Libre Texts Chemistry. (Apr. 24, 2015). 5.1: Starch and Cellulose. Chemistry LibreTexts. https://chem.libretexts.org/Bookshelves/Organic_Chemistry/Map%3A_Organic_Chemistry_(Smith)/05%3A_Stereochemistry/5.01%3A_Starch_and_Cellulose (Year: 2015).*

Sequence listing of Wichelecki WO 2018/169957 retrieved on Feb. 10, 2025 from https://patentscope.wipo.int/search/en/detail.jsf?docId=WO2018169957&_cid=P22-M6ZIAB-90853-1 (Year: 2025).*

Moradian, A., & Benner, S. A. (1992). A biomimetic biotechnological process for converting starch to fructose: thermodynamic and evolutionary considerations in applied enzymology. Journal of the American Chemical Society, 114(18), 6980-6987. (Year: 1992).*

Translation of DE102017002252A retrieved on Jul. 31, 2025 from Espacenet at https://worldwide.espacenet.com/patent/search/family/063258442/publication/DE102017002252A1?q=pn%3DDE102017002252A1 (Year: 2025).*

Sutiono, S. (2016). Enzyme engineering of a haloacid dehalogenase-like phosphatase from Thermotoga neopolitana for optimization of substrate specificity [Student publication for Master's degree]. (Year: 2016).*

Notice of Reasons for Rejection for related Japanese Application No. 2022-538439, dated Dec. 3, 2024, 13 pages.

Office Action for related Russian Application No. 2022116548/10(034938), dated Sep. 27, 2024, 19 pages.

(Continued)

*Primary Examiner* — Louise W Humphrey
*Assistant Examiner* — Kimberly C. Breen
(74) *Attorney, Agent, or Firm* — DITTHAVONG, STEINER & MLOTKOWSKI

(57) ABSTRACT

The present invention relates to a method for converting at least one oligo- and/or polysaccharide into fructose comprising the steps of: a) adding to a composition comprising water, phosphate and at least one oligo- and/or polysaccharide at least four enzymes, and b) subsequently enzymatically converting the at least one oligo- and/or polysaccharide to fructose in the presence of the at least four enzymes, wherein in step a) at least one additional saccharide is added, whereby the at least one additional saccharide is selected from the group consisting of saccharides comprising 20 or less monosaccharide residues and/or combinations thereof; wherein in step a) the at least four enzymes, preferably at least five enzymes, are selected from the group consisting of transferases, phosphorylases, mutases, isomerases, hydrolases, phosphatases and combinations thereof; and wherein at least one enzyme in step a) is a phosphatase.

10 Claims, 9 Drawing Sheets

Specification includes a Sequence Listing.

(56) References Cited

OTHER PUBLICATIONS

Zhou et al., "One-Pot Biosynthesis of High-Concentration a-Glucose 1-Phosphate from Starch by Sequential Addition of Three Hyperthermophilic Enzymes", Journal of Agricultural and Food Chemistry, vol. 64, No. 8, Mar. 2, 2016, 3 pages.
Database UniProt, "Phosphorylated Carbohydrates Phosphatase TM_1254", retrieved from EBI accession No. UniProt:Q9X0Y1, Jun. 21, 2005, 4 pages.
Kuznetsova et al., "Enzyme genomics: Application of general enzymatic screens to discover new enzymes", FEMS Microbiology Reviews, vol. 29, No. 2, Apr. 1, 2005, pp. 263-279.
International Search Report and Written Opinion of the International Searching Authority for related International Application No. PCT/EP2020/087480, dated Apr. 19, 2021, 13 pages.
Office Action for related Japanese Application No. 2022-538439, dated Apr. 1, 2025, 5 pages.
Office Action for related Egyptian Application No. 2022060837, dated Mar. 25, 2025, 10 pages.
Translation of Office Action for related Russian Application No. 2022116548/10(034938), dated Feb. 10, 2025, 6 pages.
Office Action with google translation for related Chinese Application No. 202080095806.7 dated Mar. 11, 2025, 12 pages.
Office Action for related Colombian Application No. NC2022/0010048, dated Sep. 22, 2025, 24 pages.
Office Action for related Russian U.S. Appl. No. 20/116,548/10(034938), dated Jun. 24, 2025, 11 pages.
Itolmai et al., Visual Biochemistry: Translated from German—Moscow: Mir, 2000, pp. 44-45, with machine translation.
Office Action for related Korean Application No. 10-2022-7024480, dated Jul. 21, 2025, 11 pages.
Office Action for related Japanese Application No. 2025-031158, dated Feb. 24, 2026, 9 pages.
Office Action for related Ukrainian Application No. a 2022 02112, dated Apr. 3, 2026, 22 pages.

* cited by examiner

SEQUENCE LISTING

```
<160> NUMBER OF SEQ ID NOS: 52

<210> SEQ ID NO 1
<211> LENGTH: 475
<212> TYPE: PRT
<213> ORGANISM: Bacillus flavocaldarius KP 1228
<220> FEATURE:
<223> OTHER INFORMATION: Pullulanase

<400> SEQUENCE: 1

Met Ala Trp Tyr Glu Gly Ala Phe Phe Tyr Gln Ile Phe Pro Asp Arg
1               5                   10                  15

Phe Phe Arg Ala Gly Pro Pro Gly Arg Pro Ala Pro Ala Gly Pro Phe
            20                  25                  30

Glu Pro Trp Glu Asp Pro Pro Thr Leu Arg Gly Phe Lys Gly Gly Thr
        35                  40                  45

Leu Trp Gly Val Ala Glu Lys Leu Pro Tyr Leu Leu Asp Leu Gly Val
    50                  55                  60

Glu Ala Ile Tyr Leu Asn Pro Val Phe Ala Ser Thr Ala Asn His Arg
65                  70                  75                  80

Tyr His Thr Val Asp Tyr Phe Gln Val Asp Pro Ile Leu Gly Gly Asn
                85                  90                  95

Glu Ala Leu Arg Tyr Leu Leu Glu Val Ala His Ala His Gly Val Arg
            100                 105                 110

Val Ile Leu Asp Gly Val Phe Asn His Thr Gly Arg Gly Phe Phe Ala
        115                 120                 125
```

```
Phe Gln His Leu Met Glu Asn Gly Glu Gln Ser Pro Tyr Arg Asp Trp
    130                 135                 140

Tyr His Val Lys Gly Phe Pro Leu Lys Ala Tyr Thr Ala His Pro Asn
145                 150                 155                 160

Tyr Glu Ala Trp Trp Gly Asn Pro Glu Leu Pro Lys Leu Lys Val Glu
                165                 170                 175

Thr Pro Ala Val Arg Glu Tyr Leu Leu Ala Val Ala Glu His Trp Ile
            180                 185                 190

Arg Phe Gly Val Asp Gly Trp Arg Leu Asp Val Pro Asn Glu Ile Pro
        195                 200                 205

Asp Pro Thr Phe Trp Arg Glu Phe Arg Gln Arg Val Lys Gly Ala Asn
    210                 215                 220

Pro Glu Ala Tyr Ile Val Gly Glu Ile Trp Glu Glu Ala Asp Phe Trp
225                 230                 235                 240

Leu Gln Gly Asp Met Phe Asp Ala Val Met Asn Tyr Pro Leu Ala Arg
                245                 250                 255

Ala Val Leu Gly Phe Val Gly Gly Glu Ala Leu Asp Arg Asp Leu Ala
            260                 265                 270

Ala Gln Thr Gly Leu Gly Arg Ile Glu Pro Leu Gln Ala Leu Ala Phe
        275                 280                 285

Ser His Arg Leu Glu Asp Leu Phe Gly Arg Tyr Arg Pro Glu Val Val
    290                 295                 300

Arg Ala Gln Met Asn Leu Leu Thr Ser His Asp Thr Pro Arg Leu Leu
305                 310                 315                 320

Ser Leu Met Arg Gly Ser Val Glu Arg Ala Arg Leu Ala Leu Ala Leu
                325                 330                 335

Leu Phe Leu Leu Pro Gly Asn Pro Thr Val Tyr Tyr Gly Glu Glu Val
            340                 345                 350

Gly Met Ala Gly Gly Lys Asp Pro Glu Asn Arg Gly Gly Met Val Trp
        355                 360                 365

Glu Glu Ala Arg Trp Gln Lys Asp Leu Arg Glu Thr Val Lys Arg Leu
    370                 375                 380

Ala Arg Leu Arg Lys Glu His Pro Ala Leu Arg Thr Ala Pro Tyr Leu
385                 390                 395                 400

Arg Ile Tyr Ala Gln Asp Gly His Leu Ala Phe Ala Arg Gly Pro Tyr
                405                 410                 415

Leu Val Val Val Asn Ala Ser Pro His Pro Phe Arg Gln Asp Phe Pro
            420                 425                 430

Leu His Gly Val Phe Pro Arg Gly Gly Arg Ala Val Asp Leu Leu Ser
        435                 440                 445

Gly Glu Val Cys Thr Pro Gln Gly Gly Arg Leu Cys Gly Pro Val Leu
    450                 455                 460

Pro Pro Phe Ser Leu Ala Leu Trp Arg Glu Ala
465                 470                 475


<210> SEQ ID NO 2
<211> LENGTH: 1428
<212> TYPE: DNA
<213> ORGANISM: Bacillus flavocaldarius KP 1228
<220> FEATURE:
<223> OTHER INFORMATION: coding for Pullulanase

<400> SEQUENCE: 2

atggcatggt atgaaggtgc ctttttctat cagatttttc cggatcgttt ttttcgtgca      60

ggtccgcctg gtcgtccggc accggcaggt ccgtttgaac cgtgggaaga tccgcctaca     120
```

```
ctgcgtggtt ttaaaggtgg caccctgtgg ggtgttgcag aaaaactgcc gtatctgctg    180

gatctgggtg ttgaagcaat ttatctgaat ccggtttttg caagcaccgc caatcatcgt    240

tatcataccg ttgattattt tcaggtggac ccgattcttg gtggtaatga agcactgcgt    300

tacctgctgg aagttgcaca tgcacatggt gttcgtgtta ttctggatgg tgtttttaat    360

cataccggtc gtggtttttt tgcctttcag catctgatgg aaaatggtga acagagcccg    420

tatcgtgatt ggtatcatgt taaaggtttt ccgctgaaag catataccgc acatccgaat    480

tatgaagcat ggtggggtaa tccggaactg ccgaaactga aagttgaaac accggcagtt    540

cgtgaatatt tactggcagt tgcagaacat tggattcgtt ttggtgttga tggttggcgt    600

ctggatgttc cgaatgaaat tcctgatccg accttttggc gtgaatttcg tcagcgtgtg    660

aaaggtgcaa atccggaagc atatattgtt ggcgaaattt gggaagaagc agatttttgg    720

ctgcagggtg atatgtttga tgccgttatg aattatccgc tggcacgtgc agttctgggt    780

tttgttggtg gtgaagccct ggatcgtgat ctggcagcac agacaggtct gggtcgtatt    840

gaaccgctgc aggcactggc atttagccat cgtctggaag atttatttgg tcgttatcgt    900

ccggaagttg ttcgtgcaca gatgaatctg ctgaccagcc atgatacacc gcgtctgctg    960

agcctgatgc gtggtagcgt tgaacgtgcc cgtctggcac tggccctgct gtttctgctg   1020

cctggtaatc cgaccgttta ttatggtgaa gaggttggta tggcaggcgg taaagatcct   1080

gaaaatcgtg gtggtatggt gtgggaagaa gcccgttggc agaaagatct gcgtgaaacc   1140

gttaaacgcc tggcacgtct gcgtaaagaa catccggcac tgcgtaccgc accttatctg   1200

cgtatttatg cacaggatgg tcatctggca tttgcacgtg gtccgtatct ggttgttgtt   1260

aatgcaagtc cgcatccgtt tcgtcaggat tttcctctgc atggtgtgtt tccgcgtggt   1320

ggtcgtgcag ttgatctgct gagtggtgaa gtttgtacac cgcaaggtgg tcgtctgtgt   1380

ggtccggttc tgcctccgtt tagcctggca ctgtggcgtg aagcataa                1428
```

<210> SEQ ID NO 3
<211> LENGTH: 501
<212> TYPE: PRT
<213> ORGANISM: Meiothermus ruber DSM 1279
<220> FEATURE:
<223> OTHER INFORMATION: alpha-Glucanotransferase

<400> SEQUENCE: 3

```
Met Gln Leu Gln Arg Ala Phe Gly Ile Leu Leu His Pro Thr Ser Phe
1               5                   10                  15

Pro Gly Arg Trp Gly Ile Gly Ala Leu Gly Arg Glu Ala Glu Arg Phe
            20                  25                  30

Leu Asp Trp Leu Ala Asp Ala Gly Ala Arg Trp Trp Gln Val Leu Pro
        35                  40                  45

Leu Gly Pro Thr Ser Tyr Gly Asp Ser Pro Tyr Gln Ser Phe Ser Ala
    50                  55                  60

Phe Ala Gly Asn Pro Tyr Leu Val Asp Pro Glu Met Leu Ile Glu Lys
65                  70                  75                  80

Gly Trp Leu Glu Gln Ser Glu Ala Pro Pro Pro Tyr Pro Thr Gln Arg
                85                  90                  95

Val Asp Tyr Gly Trp Leu Tyr Gln Thr Arg Trp Pro Leu Leu Arg Arg
            100                 105                 110

Ala Phe Ala Gly Phe Arg Ala Arg Ala Ser Ala Gln Asp Lys Thr Arg
        115                 120                 125
```

```
Leu Glu Ala Phe Ile Glu Ala Glu Arg Phe Trp Leu Glu Asp Tyr Ala
    130                 135                 140

Leu Phe Met Ala Leu Lys Thr Arg Phe Asp Gly Lys Pro Trp Asn Glu
145                 150                 155                 160

Trp Ser Pro Glu Leu Arg Asp Arg Glu Pro Ala Ala Leu Ala Arg Ala
                165                 170                 175

Arg Glu Glu Leu Ala Glu Glu Val Ala Leu Tyr Glu Trp Ile Gln Trp
            180                 185                 190

Leu Phe Tyr Leu Glu Trp Gly Gln Thr Lys Ala Tyr Ala Glu Ser Lys
        195                 200                 205

Gly Ile Gln Ile Ile Gly Asp Met Pro Ile Phe Val Ala Phe Asp Ser
    210                 215                 220

Ser Asp Val Trp Ala Asn Pro Gln Tyr Phe Tyr Leu Glu Ala Asp Gly
225                 230                 235                 240

Asn Pro Thr Val Val Ala Gly Val Pro Pro Asp Tyr Phe Ser Glu Thr
                245                 250                 255

Gly Gln Leu Trp Gly Asn Pro Leu Tyr Arg Trp Asp Val Met Glu Arg
            260                 265                 270

Asp Asn Phe Ala Trp Trp Ile Ala Arg Ile Arg Gln Ser Leu Lys Gln
        275                 280                 285

Cys His Leu Val Arg Ile Asp His Phe Arg Gly Phe Glu Ala Tyr Trp
    290                 295                 300

Glu Val Pro Phe Gly Arg Pro Asn Ala Val Glu Gly Arg Trp Val Lys
305                 310                 315                 320

Ala Pro Gly Glu Lys Leu Phe Ala Ala Val Arg Ala Gln Leu Ser Asp
                325                 330                 335

Ala Pro Ile Ile Ala Glu Asp Leu Gly Val Ile Thr Pro Glu Val Glu
            340                 345                 350

Ala Leu Arg Asp Gly Phe Gly Phe Pro Gly Met Lys Ile Leu Gln Phe
        355                 360                 365

Ala Phe Ser Gly Glu Asp Asn Ala Phe Leu Pro His Asn Tyr Pro Ala
    370                 375                 380

His Gly Asn Val Val Val Tyr Ser Gly Thr His Asp Asn Asp Thr Thr
385                 390                 395                 400

Leu Gly Trp Phe Arg Thr Ala Pro Glu Ala Glu Arg Ala Phe Met Arg
                405                 410                 415

Ala Tyr Leu Ala Arg Tyr Gly Ile Arg Cys Leu Ser Glu Tyr Glu Val
            420                 425                 430

Ala Gly Ala Leu Ile Glu Leu Ala Phe Lys Ser Pro Ala Lys Leu Ala
        435                 440                 445

Ile Val Pro Leu Gln Asp Val Leu Gly Leu Gly Pro Glu Ala Arg Met
    450                 455                 460

Asn Phe Pro Gly Arg Leu Gly Asp Asn Trp Ala Trp Arg Tyr Ala Glu
465                 470                 475                 480

Gly Asp Leu Glu Pro Gly Leu Ala Ala Gly Leu Arg Ala Leu Ala Glu
                485                 490                 495

Ala Ser Gln Arg Ala
            500
```

<210> SEQ ID NO 4
<211> LENGTH: 1506
<212> TYPE: DNA
<213> ORGANISM: Meiothermus ruber DSM 1279
<220> FEATURE:
<223> OTHER INFORMATION: coding for alpha-Glucanotransferase

<400> SEQUENCE: 4

```
atgcaactcc aacgcgcttt tggaattttg ctccacccca ccagttttcc gggtcgctgg     60
gggattgggg ctctgggccg cgaggccgag cggtttttgg actggctggc cgatgcggga    120
gcccgctggt ggcaggtctt accgctgggc cctaccagtt acggcgactc gccgtaccag    180
tccttctcgg cttttgccgg taacccgtat ttggttgacc ccgagatgct gattgaaaaa    240
ggctggctgg aacaaagcga agcgcccccg ccgtatccga cccagcgcgt ggattatggc    300
tggctttacc agacccgctg gcccctgttg cggcgggctt tcgcggggtt tcgggcaagg    360
gcttcggccc aggataagac ccgactggaa gcctttatcg aggccgagcg cttctggctg    420
gaagactatg cgctctttat ggccctcaag acccggtttg acggcaagcc ctggaacgag    480
tggagccccg agctgcgcga ccgtgaaccg gctgccctgg ccagggcccg tgaggagctg    540
gccgaggagg tggcccttta cgagtggatt cagtggcttt tttatctgga atggggccag    600
accaaggcct atgccgaatc caaggggatt cagattatcg gcgatatgcc catctttgtg    660
gccttcgatt cctcagatgt ctgggccaac ccgcagtact tctacctcga ggccgatggc    720
aaccccacgg tggtggcggg cgttccgccg gactacttct ccgaaaccgg ccagctctgg    780
ggcaatccgc tctatcgctg ggatgtgatg gaaagggaca actttgcctg gtggattgcc    840
cgcataaggc agtcgctcaa gcagtgccac ctggtgcgca tcgaccactt ccgcgggttt    900
gaagcctact gggaggttcc gtttggccgg cccaatgctg tggaggggcg ctgggtcaaa    960
gccccagggg agaagctgtt tgctgcggtg cgggcccaac tgagcgatgc gcccatcatt   1020
gccgaagacc tgggggtgat cacccccgag gtggaggctt tgcgcgatgg cttcgggttc   1080
cccggcatga agattttgca gtttgctttt tccggtgagg acaacgcctt tttgccccac   1140
aactaccccg cgcacggcaa tgtggtggtg tacagcggaa cccacgacaa cgacaccacc   1200
ctgggatggt tccgcaccgc gccggaggcc gagcgggcct tcatgcgggc ctacctggcc   1260
cgctatggca tccgttgttt gtcggaatac gaggtcgcgg gcgctttgat cgagctggcc   1320
ttcaaaagcc cggccaagct ggctattgtg cctttgcagg acgtgctggg gctgggcccc   1380
gaggcccgca tgaacttccc cggacggctg gggacaact gggcgtggcg ctacgccgaa    1440
ggcgacctcg agcccggtct ggccgcggga ctgcgggccc tggccgaggc cagccagcgc   1500
gcttga                                                              1506
```

<210> SEQ ID NO 5
<211> LENGTH: 822
<212> TYPE: PRT
<213> ORGANISM: Thermotoga naphthophila DSM 13996
<220> FEATURE:
<223> OTHER INFORMATION: alpha-Glucan Phosphorylase

<400> SEQUENCE: 5

```
Met Leu Glu Lys Leu Pro Glu Asn Leu Lys Glu Leu Glu Ser Leu Ala
1               5                   10                  15

Tyr Asn Leu Trp Trp Ser Trp Ser Arg Pro Ala Gln Arg Leu Trp Arg
            20                  25                  30

Met Ile Asp Ser Glu Lys Trp Glu Glu His Arg Asn Pro Val Lys Ile
        35                  40                  45

Leu Arg Glu Val Ser Lys Glu Arg Leu Glu Glu Leu Ser Lys Asp Glu
    50                  55                  60

Asp Phe Ile Ala Leu Tyr Glu Leu Thr Leu Glu Arg Phe Thr Asp Tyr
65                  70                  75                  80
```

```
Met Glu Arg Glu Asp Thr Trp Phe Asn Val Asn Tyr Pro Glu Trp Asp
                85                  90                  95

Glu Lys Ile Val Tyr Met Cys Met Glu Tyr Gly Leu Thr Lys Ala Leu
            100                 105                 110

Pro Ile Tyr Ser Gly Gly Leu Gly Ile Leu Ala Gly Asp His Leu Lys
        115                 120                 125

Ser Ala Ser Asp Leu Gly Leu Pro Leu Ile Ala Val Gly Leu Leu Tyr
    130                 135                 140

Lys His Gly Tyr Phe Thr Gln Gln Ile Asp Ser Asp Gly Arg Gln Ile
145                 150                 155                 160

Glu Ile Phe Pro Glu Tyr Asp Ile Glu Glu Leu Pro Met Lys Pro Leu
                165                 170                 175

Arg Asp Glu Asp Gly Asn Gln Val Ile Val Glu Val Pro Ile Asp Asn
            180                 185                 190

Asp Thr Val Lys Ala Arg Val Phe Glu Val Gln Val Gly Arg Val Lys
        195                 200                 205

Leu Tyr Leu Leu Asp Thr Asp Phe Glu Glu Asn Glu Asp Arg Phe Arg
    210                 215                 220

Lys Ile Cys Asp Tyr Leu Tyr Asn Pro Glu Pro Asp Val Arg Val Ser
225                 230                 235                 240

Gln Glu Ile Leu Leu Gly Ile Gly Gly Met Lys Leu Leu Lys Thr Leu
                245                 250                 255

Lys Ile Lys Pro Gly Val Ile His Leu Asn Glu Gly His Pro Ala Phe
            260                 265                 270

Ser Ser Leu Glu Arg Ile Lys Ser Tyr Met Glu Glu Gly Tyr Ser Phe
        275                 280                 285

Thr Glu Ala Leu Glu Ile Val Arg Gln Thr Thr Val Phe Thr Thr His
    290                 295                 300

Thr Pro Val Pro Ala Gly His Asp Arg Phe Pro Phe Asp Phe Val Glu
305                 310                 315                 320

Lys Lys Leu Thr Lys Phe Phe Glu Gly Phe Glu Ser Lys Glu Leu Leu
                325                 330                 335

Met Asn Leu Gly Lys Asp Glu Asp Gly Asn Phe Asn Met Thr Tyr Leu
            340                 345                 350

Ala Leu Arg Thr Ser Ser Phe Ile Asn Gly Val Ser Lys Leu His Ala
        355                 360                 365

Asp Val Ser Arg Arg Met Phe Lys Asn Val Trp Lys Gly Val Pro Val
    370                 375                 380

Glu Glu Ile Pro Ile Glu Gly Ile Thr Asn Gly Val His Met Gly Thr
385                 390                 395                 400

Trp Ile Asn Arg Glu Met Arg Lys Leu Phe Asp Arg Tyr Leu Gly Arg
                405                 410                 415

Val Trp Arg Glu His Thr Asp Leu Glu Gly Ile Trp Tyr Gly Val Asp
            420                 425                 430

Arg Ile Pro Asp Glu Glu Leu Trp Glu Ala His Leu Asn Ala Lys Lys
        435                 440                 445

Arg Phe Ile Asp Tyr Ile Arg Glu Ser Ile Lys Arg Arg Asn Glu Arg
    450                 455                 460

Leu Gly Ile Asn Glu Pro Leu Pro Glu Ile Ser Glu Asn Val Leu Ile
465                 470                 475                 480

Ile Gly Phe Ala Arg Arg Phe Ala Thr Tyr Lys Arg Ala Val Leu Leu
                485                 490                 495
```

```
Phe Ser Asp Leu Glu Arg Leu Lys Arg Ile Val Asn Asn Ser Glu Arg
            500                 505                 510

Pro Val Tyr Ile Val Tyr Ala Gly Lys Ala His Pro Arg Asp Glu Gly
        515                 520                 525

Gly Lys Glu Phe Leu Arg Arg Ile Tyr Glu Val Ser Gln Met Pro Asp
    530                 535                 540

Phe Lys Asn Lys Ile Ile Val Leu Glu Asn Tyr Asp Ile Gly Met Ala
545                 550                 555                 560

Arg Leu Met Val Ser Gly Val Asp Val Trp Leu Asn Asn Pro Arg Arg
                565                 570                 575

Pro Met Glu Ala Ser Gly Thr Ser Gly Met Lys Ala Ala Ala Asn Gly
            580                 585                 590

Val Leu Asn Ala Ser Val Tyr Asp Gly Trp Trp Val Glu Gly Tyr Asn
        595                 600                 605

Gly Arg Asn Gly Trp Val Ile Gly Asp Glu Ser Val Leu Pro Glu Thr
    610                 615                 620

Glu Ala Asp Asp Pro Lys Asp Ala Glu Ala Leu Tyr Glu Leu Leu Glu
625                 630                 635                 640

Asn Glu Ile Ile Pro Thr Tyr Tyr Glu Asn Arg Glu Lys Trp Ile Phe
                645                 650                 655

Met Met Lys Glu Ser Ile Lys Ser Val Ala Pro Lys Phe Ser Thr Thr
            660                 665                 670

Arg Met Leu Lys Glu Tyr Thr Glu Lys Phe Tyr Ile Lys Gly Leu Val
        675                 680                 685

Asn Arg Glu Trp Leu Glu Arg Arg Glu Asn Val Glu Lys Ile Gly Ala
    690                 695                 700

Trp Lys Glu Arg Ile Leu Lys Asn Trp Glu Asn Val Ser Ile Glu Arg
705                 710                 715                 720

Ile Val Leu Glu Asp Ser Lys Ser Val Glu Val Thr Val Lys Leu Gly
                725                 730                 735

Asp Leu Thr Pro Asn Asp Val Ile Val Glu Leu Val Ala Gly Arg Gly
            740                 745                 750

Glu Gly Met Glu Asp Leu Glu Val Trp Lys Val Ile His Ile Arg Arg
        755                 760                 765

Tyr Arg Lys Glu Asn Asp Leu Phe Val Tyr Thr Tyr Thr Asn Gly Val
    770                 775                 780

Leu Gly His Leu Gly Ser Pro Gly Trp Phe Tyr Ala Val Arg Val Ile
785                 790                 795                 800

Pro Tyr His Pro Arg Leu Pro Ile Lys Phe Leu Pro Glu Val Pro Val
                805                 810                 815

Val Trp Lys Lys Val Leu
            820
```

<210> SEQ ID NO 6
<211> LENGTH: 2469
<212> TYPE: DNA
<213> ORGANISM: Thermotoga naphthophila DSM 13996
<220> FEATURE:
<223> OTHER INFORMATION: coding for alpha-Glucan Phosphorylase

<400> SEQUENCE: 6

```
atgctggaga aacttcccga gaacctgaaa gagctcgaga gccttgccta caacctctgg     60

tggagctggt ccagacctgc tcagagactc tggagaatga tcgattcaga aaagtgggag    120

gaacacagaa atcccgtcaa aatactgaga gaagtctcaa aggaaagact ggaagaacta    180
```

-continued

```
tcgaaagacg aggacttcat cgctctctac gaactgacgc tcgagagatt cacagactac    240
atggaaaggg aagacacctg gttcaacgtg aactatcccg aatgggacga aaagatagtt    300
tacatgtgta tggaatacgg actgacgaaa gcacttccga tctactctgg aggactcggt    360
atccttgccg gagaccacct caaatcagcc agtgatcttg gccttcctct catagccgta    420
ggtcttcttt acaaacacgg gtatttcact caacagatag acagtgacgg aagacagatc    480
gagatctttc cagaatacga catcgaagaa ctcccgatga aacctctcag ggatgaagac    540
ggaaaccagg tgatcgtaga agtacccata gacaacgata ctgtaaaagc gcgtgtgttc    600
gaggtacagg tcggaagggt gaaactgtat cttctcgaca ctgacttcga ggaaaacgag    660
gatagattca gaaagatctg cgactatctc tacaatcccg agcctgatgt gagagtttcc    720
caggaaattc tgctcggcat tggtggaatg aaactcctga agactctcaa gataaaacct    780
ggagtcatcc acctgaacga aggtcatccc gctttttcat ccctcgaaag gataaagagc    840
tacatggaag aaggatattc cttcaccgag gcccttgaga tcgtcagaca gaccacagtt    900
ttcacgacac acacccccgt ccccgcaggt cacgacaggt tcccgttcga tttcgtggaa    960
aagaagctga caaagttctt cgaaggattc gaatccaaag aactgcttat gaaccttgga   1020
aaagacgaag acggaaattt caacatgacg tatcttgctt tgagaacctc ctcctttata   1080
aacggagtga gcaaacttca cgctgacgta tcgagaagga tgttcaaaaa tgtctggaag   1140
ggagttccgg tggaggagat ccccattgaa ggcatcacga atggtgtcca catgggaacc   1200
tggatcaacc gcgagatgag aaaactgttc gacaggtacc tcggtagagt ctggagggaa   1260
cacactgacc tcgaaggaat atggtacgga gttgacagaa tacccgatga agaactctgg   1320
gaagcgcatc tgaacgcaaa gaaacgattc atagattaca taagagaatc catcaaaagg   1380
agaaacgaaa ggcttggaat caacgaacca ctgccggaga tcagtgaaaa cgtgctcatc   1440
ataggttttg ccagaaggtt cgcaacttac aagagagccg tcctgctctt cagcgatctg   1500
gaaagactca agagaattgt caataattcc gagaggccgg tttacattgt gtacgctgga   1560
aaggcccacc cgagagacga aggtggaaag gagtttctca gaaggatcta cgaagtttca   1620
cagatgcccg atttcaagaa caaaatcatc gtactcgaaa actatgacat cggaatggct   1680
cgactcatgg tgtcgggtgt tgacgtgtgg ttgaacaatc caaggaggcc catggaggca   1740
agcgggacaa gtggtatgaa agctgcagcg aacggtgttc tgaacgcgag tgtatacgat   1800
ggctggtggg ttgagggata caacggcaga aacggatggg tgataggtga tgaaagcgtg   1860
cttccagaaa cagaagcgga tgatccaaag gatgccgagg ctctgtatga gcttctcgaa   1920
aacgaaataa tccccaccta ctacgaaaac agagaaaagt ggatcttcat gatgaaagaa   1980
agcataaaga gcgtggctcc aaaattcagc accacccgca tgctcaaaga gtacacggag   2040
aaattctaca taaagggact tgtgaacagg gaatggctgg agagaagaga aaacgtcgaa   2100
aaaatcggag cctggaaaga aagaatcctc aagaactggg agaatgtttc catagagcgc   2160
atcgttcttg aagattcgaa gagcgtagaa gtaactgtaa aactgggcga tctcacaccg   2220
aacgacgtga tagtcgaact tgtggctgga agaggagagg gaatggaaga tctcgaagtg   2280
tggaaagtga tacacatcag aaggtacagg aaagagaacg atctattcgt ttacacttac   2340
accaatggtg ttcttggtca tcttggatct cccggatggt tctacgcggt gagagtcata   2400
ccgtaccatc ccaggcttcc catcaagttc ctgcccgaag taccggttgt ctggaagaag   2460
gttctctga                                                           2469
```

<210> SEQ ID NO 7
<211> LENGTH: 455
<212> TYPE: PRT
<213> ORGANISM: Saccharolobus solfataricus
<220> FEATURE:
<223> OTHER INFORMATION: Phosphoglucomutase

<400> SEQUENCE: 7

```
Met Gly Lys Leu Phe Gly Thr Asp Gly Ile Arg Gly Val Thr Asn Thr
1               5                   10                  15

Glu Leu Gln Pro Glu Phe Ala Leu Lys Ile Gly Lys Ala Ile Gly Thr
            20                  25                  30

Tyr Phe Gly Lys Gly Ala Arg Ile Leu Ile Gly Arg Asp Val Arg Ala
        35                  40                  45

Gly Gly Asp Met Leu Leu Lys Ala Val Glu Ser Gly Leu Leu Ser Ser
    50                  55                  60

Gly Val Leu Val Tyr Glu Ala Gly Met Ala Pro Thr Pro Ala Phe Gln
65                  70                  75                  80

Tyr Gly Val Lys Ala Leu Gly Tyr Asp Gly Gly Val Ile Ile Thr Ala
                85                  90                  95

Ser His Asn Pro Ala Glu Tyr Asn Gly Ile Lys Val Leu Ser Pro His
            100                 105                 110

Gly Ile Glu Ile Ser Arg Glu Asp Glu Asp Lys Ile Glu Asp Ile Tyr
        115                 120                 125

Phe Asn Ser Arg Phe His Val Val Glu Trp Asn Gly Leu Val Asn Asp
    130                 135                 140

Val Lys Arg Glu Asp Lys Val Ile Glu Thr Tyr Leu Arg Gly Ile Leu
145                 150                 155                 160

Ser His Val Asp Thr Glu Lys Ile Lys Ser Lys Lys Tyr Lys Val Leu
                165                 170                 175

Ile Asp Pro Ala Asn Ser Val Gly Thr Leu Val Thr Pro Ile Val Ala
            180                 185                 190

Arg Glu Leu Gly Cys Lys Val Phe Thr Ile Asn Gly Asn Leu Asp Pro
        195                 200                 205

Leu Phe Ser Ala Arg Thr Pro Glu Pro Thr Phe Glu Ser Leu Thr Glu
    210                 215                 220

Ser Ala Lys Val Ala Lys Gln Leu Gly Val Asp Leu Ala Val Ala His
225                 230                 235                 240

Asp Gly Asp Ala Asp Arg Ala Ile Phe Ile Asp Ser Met Gly Arg Val
                245                 250                 255

Gln Trp Gly Asp Arg Ser Gly Thr Leu Leu Ser Tyr Trp Ala Ser Val
            260                 265                 270

Lys Ala Pro Asn Leu Pro Arg Arg Ile Phe Thr Ala Val Ser Ser Ser
        275                 280                 285

Ser Leu Val Glu Glu Tyr Leu Lys Lys Tyr Asn Ile Glu Val Lys Trp
    290                 295                 300

Thr Lys Val Gly Ser Ile Asp Ile Ala His Met Leu Phe Lys Glu Lys
305                 310                 315                 320

Gly Val Ala Gly Phe Glu Glu Asn Gly Gly Phe Met Tyr Pro Pro His
                325                 330                 335

Gln Thr Val Arg Asp Gly Ala Met Ser Phe Ala Leu Met Leu Asp Met
            340                 345                 350

Met Ala Ser Glu Asn Glu Ser Ser Ala Glu Leu Phe Asn Arg Leu Pro
        355                 360                 365

Val Tyr Tyr Leu Val Lys Thr Lys Val Arg Val Thr Glu Lys Ser Asp
```

```
    370                 375                 380

Ile Lys Lys Ile Tyr Asp Glu Val Met Asn Lys Tyr Gly Asn Tyr Gly
385                 390                 395                 400

Asn Thr Val Thr Ile Asp Gly Val Lys Ile Ile Gly Ser Asp Phe Trp
                405                 410                 415

Leu Leu Val Arg Lys Ser Gly Thr Glu Pro Ile Ile Arg Ile Leu Val
            420                 425                 430

Glu Ala Lys Asp Glu Asn Lys Ser Lys Glu Leu Ala Lys Glu Leu Glu
        435                 440                 445

Lys Leu Val Ser Glu Leu Val
    450                 455
```

```
<210> SEQ ID NO 8
<211> LENGTH: 1368
<212> TYPE: DNA
<213> ORGANISM: Saccharolobus solfataricus
<220> FEATURE:
<223> OTHER INFORMATION: coding for Phosphoglucomutase

<400> SEQUENCE: 8

atgggtaagt tgtttggaac tgatggaata agaggagtta ccaatactga attacaacca      60

gagtttgcgt taaagattgg aaaagctata ggaacatatt ttggtaaagg tgctagaatt     120

ctaataggta gggatgtaag agcaggagga gatatgctac ttaaagctgt tgagagtgga     180

ttgttaagta gtggtgtact ggtttatgaa gcagggatgg ctcctactcc agctttccaa     240

tatggtgtga aggctttagg atatgacggt ggtgttataa taactgccag tcataatcca     300

gctgaatata atggtatcaa agtcctttct ccacacggta ttgagatatc tagagaagat     360

gaggataaga tagaagatat atactttaat agcaggtttc atgtggtaga gtggaatggt     420

ttagtaaacg atgtgaaaag agaagacaag gttattgaga cttatttaag aggtattctc     480

tctcatgttg atactgaaaa aattaagagt aaaaagtata aagttctcat agatcctgct     540

aatagtgtag gtacattagt aacgcccatt gttgcaaggg agttgggatg taaagttttt     600

actattaatg ggaatttaga tcctttattt tcagctagaa ctcctgaacc tactttcgag     660

agccttaccg aatccgcaaa agttgctaaa caattaggag ttgatttagc agtggctcat     720

gatggtgatg cagatagggc aatttttata gattccatgg gtagggtcca atggggtgat     780

aggagcggta ctctattatc atattgggcc tcggttaaag ctccaaattt acctagacgc     840

atatttactg cagtttctag ctctagcttg gttgaggagt atctgaaaaa gtataatata     900

gaggttaagt ggactaaggt aggtagcata gatattgcgc atatgttatt taaagaaaaa     960

ggagtagctg gatttgagga aaatggtggg ttcatgtatc cccctcatca gacggtaaga    1020

gatggcgcaa tgtcgttcgc cttaatgctg gatatgatgg catctgagaa cgaaagttct    1080

gctgagctat ttaatagact ccccgtttat tatttggtaa aaacgaaagt tagagttacg    1140

gaaaagagtg atataaagaa gatttatgat gaagtaatga ataagtacgg aaattacggg    1200

aatactgtta caatagatgg tgttaagatt ataggtagtg atttctggct cttggttagg    1260

aaaagtggta cggagccgat aataagaata ctagttgagg caaaagatga gaataaatct    1320

aaagaattag ctaaagaatt ggaaaagtta gtgagtgaac tagtatga                 1368
```

```
<210> SEQ ID NO 9
<211> LENGTH: 578
<212> TYPE: PRT
<213> ORGANISM: Clostridium thermocellum
<220> FEATURE:
```

<223> OTHER INFORMATION: Phosphoglucomutase

<400> SEQUENCE: 9

```
Met Arg Ser Ser Ala Leu Tyr Lys Phe Trp Val Glu Asn Asp Tyr Phe
1               5                   10                  15

Asp Ala Glu Thr Lys Lys Glu Leu Leu Ser Ile Lys Asp Asn Pro Lys
            20                  25                  30

Glu Ile Glu Glu Arg Phe Tyr Lys Asp Leu Glu Phe Gly Thr Gly Gly
        35                  40                  45

Leu Arg Gly Ile Ile Gly Ala Gly Thr Asn Arg Ile Asn Ile Tyr Thr
    50                  55                  60

Val Arg Lys Ala Ser Gln Gly Leu Ala Asp Tyr Ile Lys Ser Leu Gly
65                  70                  75                  80

Leu Gln Asp Arg Gly Ile Ala Ile Ala Tyr Asp Ser Arg Tyr Lys Ser
                85                  90                  95

Pro Glu Phe Ala Leu Glu Ala Ala Lys Val Phe Ala Gly Asn Gly Ile
            100                 105                 110

Lys Ala Phe Leu Phe Asp Glu Leu Arg Pro Thr Pro Glu Leu Ser Phe
        115                 120                 125

Thr Val Arg His Leu Asn Ala Ala Ala Gly Val Val Ile Thr Ala Ser
    130                 135                 140

His Asn Pro Lys Glu Tyr Asn Gly Tyr Lys Val Tyr Gly Glu Asp Gly
145                 150                 155                 160

Gly Gln Leu Pro Val Glu Ala Ser Asn Lys Val Ile Ser Tyr Ile Asn
                165                 170                 175

Lys Ile Glu Asp Ile Thr Gln Val Lys Val Met Glu Lys Asp Glu Ala
            180                 185                 190

Ile Glu Lys Gly Leu Leu Arg Ile Ile Gly Lys Glu Ile Asp Asp Glu
        195                 200                 205

Tyr Ile Ser Lys Leu Lys Thr Leu Ser Ala Asn Pro Glu Leu Ala Ala
    210                 215                 220

Glu Ile Gly Lys Thr Phe Lys Ile Val Tyr Thr Pro Leu His Gly Ala
225                 230                 235                 240

Gly Asn Lys Pro Val Arg Arg Ile Leu Asp Glu Ile Gly Phe Lys Asn
                245                 250                 255

Val Leu Val Val Lys Glu Gln Glu Leu Pro Asp Ser Glu Phe Ser Thr
            260                 265                 270

Val Lys Ser Pro Asn Pro Glu Glu Arg Glu Ala Phe Glu Leu Ala Ile
        275                 280                 285

Glu Leu Ala Lys Lys Glu Asn Val Asp Leu Ile Ile Gly Thr Asp Pro
    290                 295                 300

Asp Cys Asp Arg Val Gly Ile Val Val Arg Asn Lys Glu Gly Glu Tyr
305                 310                 315                 320

Val Pro Leu Thr Gly Asn Gln Thr Gly Cys Leu Leu Leu Glu Tyr Ile
                325                 330                 335

Leu Ser Gln Lys Lys Gln Arg Gly Glu Leu Pro Glu Asn Gly Phe Val
            340                 345                 350

Val Lys Thr Ile Val Thr Thr Glu Leu Ala Arg Ala Ile Thr Asp Ala
        355                 360                 365

Tyr Asn Val Glu Leu Val Glu Val Leu Thr Gly Phe Lys Phe Ile Gly
    370                 375                 380

Glu Lys Ile Lys Gln Leu Asp Glu Phe Gly Asp Lys Lys Tyr Leu Phe
385                 390                 395                 400
```

```
Gly Phe Glu Glu Ser Tyr Gly Tyr Leu Ala Gly Thr Phe Ala Arg Asp
                405                 410                 415

Lys Asp Ala Val Val Ala Ser Met Leu Ile Ala Glu Met Ala Ala Tyr
            420                 425                 430

Tyr Lys Ser Arg Gly Leu Thr Leu Tyr Glu Gly Leu Met Glu Leu Leu
        435                 440                 445

Glu Lys Tyr Gly Tyr Thr Leu Glu Gly Ile Thr Ser Phe Thr Leu Lys
    450                 455                 460

Gly Lys Asp Gly Val Glu Lys Ile Lys Ser Ala Met Lys Asn Leu Arg
465                 470                 475                 480

Glu Asn Arg Val Val Lys Phe Gly Glu Tyr Glu Ala Val Ala Val Arg
                485                 490                 495

Asp Tyr Leu Thr Ser Glu Arg Tyr Glu Val Ala Thr Gly Ala Lys Glu
            500                 505                 510

Lys Leu Thr Leu Val Glu Ser Asp Val Leu Tyr Tyr Glu Leu Lys Asp
        515                 520                 525

Lys Ala Trp Phe Cys Ile Arg Pro Ser Gly Thr Glu Pro Lys Ile Lys
    530                 535                 540

Ile Tyr Tyr Gly Val Thr Glu Lys Ser Met Asp Ala Ala Lys Glu Lys
545                 550                 555                 560

Leu Lys His Leu Gln Asp Asn Val Leu Ser Val Ile Glu Pro Leu Leu
                565                 570                 575

Lys Asp
```

<210> SEQ ID NO 10
<211> LENGTH: 1737
<212> TYPE: DNA
<213> ORGANISM: Chlostridium thermocellum
<220> FEATURE:
<223> OTHER INFORMATION: coding for Phosphoglucomutase

<400> SEQUENCE: 10

```
atgcgaagta gcgcgcttta taaattttgg gtggagaatg attattttga tgcggaaaca      60

aagaaagaac ttttgagtat taaagacaat ccgaaggaaa tagaagagag gttttacaag     120

gatttggaat ttggtaccgg cggacttagg ggaattatcg gtgccgggac caacagaatc     180

aatatttaca ccgtcagaaa agcttcccag ggacttgcgg attatataaa gagtcttgga     240

ttgcaagaca ggggaatagc aattgcttat gattcccgtt acaaatcccc ggaatttgct     300

ttggaagctg ccaaggtttt tgcgggaaac ggcataaaag cgtttctttt tgatgaattg     360

agaccaacac cggaactttc ttttaccgta aggcatttaa atgcagctgc cggtgtggtt     420

attacggcga gccataatcc caaggagtat aatggataca aagtttatgg agaagacggg     480

ggacaacttc ctgtagaggc atcaaacaaa gttatatcct atataaataa aattgaggat     540

ataactcagg ttaaggttat ggaaaaggac gaagcgatag agaagggttt gctcaggatt     600

ataggcaagg aaattgacga tgagtatata tcgaaattaa aaactctttc tgcaaaccct     660

gaactggctg cagaaatagg caaaactttc aaaatagtgt acacgccgtt gcatggcgca     720

ggaaacaaac ctgtaagaag aatacttgac gaaattggat ttaaaaatgt acttgtggtc     780

aaagaacagg agcttccgga cagcgaattt tccacggtaa aatcacccaa tccggaggaa     840

agggaagcgt ttgagcttgc cattgagctg gcaaaaaaag aaaatgttga ccttatcata     900

ggtaccgacc ctgactgtga cagagtgggt attgtcgtaa gaaacaaaga aggcgagtat     960

gtgcctctta cgggtaatca gacgggttgt ttgctgcttg agtacatact gtctcaaaag    1020
```

```
aagcaaagag gagagcttcc tgaaaacgga tttgtcgtaa agacaatagt tacaacggag   1080

cttgccagag ctattactga tgcttacaat gtggaacttg tggaagtttt gacgggattt   1140

aagtttatag gcgagaaaat taagcagctg gatgagtttg gagacaaaaa atatcttttt   1200

ggttttgaag aaagctatgg ataccttgca ggaacttttg caagagacaa ggacgctgtt   1260

gttgcatcca tgcttattgc cgaaatggcg gcttattaca aatcaagagg tctgactctt   1320

tacgagggac tgatggagtt acttgagaaa tatggataca ctcttgaagg aattacttcg   1380

tttactctca agggaaaaga cggcgtggaa aagataaagt cggctatgaa aaaccttaga   1440

gaaaacagag ttgtaaaatt tggagaatat gaagccgttg ccgtaaggga ctatttgaca   1500

agtgaacggt atgaagtggc aacgggtgcg aaagagaaac ttacacttgt tgagtcggat   1560

gtgttgtatt atgagcttaa ggataaagcc tggttctgta taagaccttc cggcacagag   1620

ccgaaaataa agatttatta tggtgttaca gaaaagagta tggatgctgc aaaagagaaa   1680

ttgaaacatt tgcaggataa tgtactgtca gttatagaac cgcttcttaa agactga      1737
```

<210> SEQ ID NO 11
<211> LENGTH: 448
<212> TYPE: PRT
<213> ORGANISM: Thermotoga maritima
<220> FEATURE:
<223> OTHER INFORMATION: Phosphoglucoisomerase

<400> SEQUENCE: 11

```
Met Ser Leu Lys Phe Asp Phe Ser Asn Leu Phe Glu Pro Asn Ile Ser
1               5                   10                  15

Gly Gly Leu Thr Asp Glu Asp Val Lys Ser Val Glu Glu Lys Val Thr
            20                  25                  30

Ser Ala Val Arg Asn Phe Val Glu Asn Thr Pro Asp Phe Ala Lys Leu
        35                  40                  45

Asp Arg Ser Trp Ile Asp Ser Val Lys Ser Leu Glu Asp Trp Ile Ile
    50                  55                  60

Asn Phe Asp Thr Val Val Val Leu Gly Ile Gly Gly Ser Gly Leu Gly
65                  70                  75                  80

Asn Leu Ala Leu His Tyr Ser Leu Arg Pro Leu Asn Trp Asn Glu Met
                85                  90                  95

Thr Arg Glu Glu Arg Asn Gly Tyr Ala Arg Val Phe Val Val Asp Asn
            100                 105                 110

Val Asp Pro Asp Leu Met Ser Ser Val Leu Asp Arg Ile Asp Pro Lys
        115                 120                 125

Thr Thr Leu Phe Asn Val Ile Ser Lys Ser Gly Ser Thr Ala Glu Val
    130                 135                 140

Met Ala Thr Tyr Ser Ile Ala Arg Gly Ile Leu Glu Ala Tyr Gly Leu
145                 150                 155                 160

Asp Pro Arg Glu His Met Leu Ile Thr Thr Asp Pro Glu Lys Gly Phe
                165                 170                 175

Leu Arg Lys Leu Val Lys Glu Glu Gly Phe Arg Ser Leu Glu Val Pro
            180                 185                 190

Pro Gly Val Gly Gly Arg Phe Ser Val Leu Thr Pro Val Gly Leu Leu
        195                 200                 205

Ser Ala Met Ala Glu Gly Ile Asp Ile Asp Glu Leu His Glu Gly Ala
    210                 215                 220

Lys Asp Ala Phe Glu Lys Ser Met Lys Glu Asn Ile Leu Glu Asn Pro
225                 230                 235                 240
```

```
Ala Ala Met Ile Ala Leu Thr His Tyr Leu Tyr Leu Asn Lys Gly Lys
                245                 250                 255

Ser Ile Ser Val Met Met Ala Tyr Ser Asn Arg Met Ile Tyr Leu Val
            260                 265                 270

Asp Trp Tyr Arg Gln Leu Trp Ala Glu Ser Leu Gly Lys Arg Tyr Asn
        275                 280                 285

Leu Lys Gly Glu Glu Val Phe Thr Gly Gln Thr Pro Val Lys Ala Leu
    290                 295                 300

Gly Ala Thr Asp Gln His Ser Gln Ile Gln Leu Tyr Asn Glu Gly Pro
305                 310                 315                 320

Asn Asp Lys Val Ile Thr Phe Leu Arg Val Glu Asn Phe Asp Arg Glu
                325                 330                 335

Ile Val Ile Pro Glu Thr Gly Arg Ala Glu Leu Ser Tyr Leu Ala Arg
            340                 345                 350

Lys Lys Leu Ser Glu Leu Leu Leu Ala Glu Gln Thr Gly Thr Glu Glu
        355                 360                 365

Ala Leu Arg Glu Asn Asn Arg Pro Asn Met Arg Val Thr Phe Asp Gly
    370                 375                 380

Leu Thr Pro Tyr Asn Val Gly Gln Phe Phe Ala Tyr Tyr Glu Ala Ala
385                 390                 395                 400

Thr Ala Phe Met Gly Tyr Leu Leu Glu Ile Asn Pro Phe Asp Gln Pro
                405                 410                 415

Gly Val Glu Leu Gly Lys Lys Ile Thr Phe Ala Leu Met Gly Arg Glu
            420                 425                 430

Gly Tyr Thr Tyr Glu Ile Lys Glu Arg Ser Lys Lys Val Ile Ile Glu
        435                 440                 445
```

<210> SEQ ID NO 12
<211> LENGTH: 1347
<212> TYPE: DNA
<213> ORGANISM: Thermotoga maritima
<220> FEATURE:
<223> OTHER INFORMATION: coding for Phosphoglucoisomerase

<400> SEQUENCE: 12

```
atgagcctga aatttgattt tagcaacctg tttgaaccga atattagcgg tggtctgacc      60

gatgaagatg ttaaaagcgt ggaagaaaaa gttaccagcg cagtgcgtaa ttttgttgaa     120

aacacaccgg attttgcaaa actggatcgt agctggattg atagcgtgaa aagcctggaa     180

gattggatca ttaactttga taccgttgtt gttctgggta ttggtggtag cggtctgggt     240

aatctggcac tgcattatag cctgcgtccg ctgaattgga atgaaatgac ccgtgaagaa     300

cgtaatggtt atgcccgtgt gtttgttgtt gataatgtgg atccggatct gatgagcagc     360

gttctggatc gtattgatcc gaaaaccacc ctgtttaacg ttattagcaa aagcggtagc     420

accgcagaag ttatggcaac ctatagcatt gcacgtggta ttctggaagc ctatggtctg     480

gatccgcgtg aacacatgct gattaccacc gatccggaaa aaggttttct gcgcaaactg     540

gtgaaagaag aaggttttcg tagcctggaa gttccgcctg gtgttggtgg tcgttttagc     600

gttctgacac cggttggtct gctgagcgca atggcagaag gtattgatat cgacgaactg     660

catgaaggtg caaaagatgc ctttgaaaaa agcatgaaag aaaacatcct ggaaaatccg     720

gcagcaatga ttgcactgac ccattatctg tatctgaaca aaggcaaaag cattagcgtt     780

atgatggcct atagcaaccg tatgatttat ctggttgatt ggtatcgtca gctgtgggca     840

gaaagcctgg gtaaacgcta taatctgaaa ggcgaagaag tttttaccgg tcagacaccg     900
```

```
gttaaagcac tgggtgcaac cgatcagcat agccagattc agctgtataa tgaaggtccg    960

aacgataaag ttattacctt tctgcgcgtg gaaaattttg atcgcgaaat tgttattccg   1020

gaaaccggtc gtgcagaact gagctatctg gcacgtaaaa aactgagcga actgctgctg   1080

gcagaacaga ccggcaccga agaagcactg cgcgaaaaca atcgtccgaa tatgcgtgtt   1140

acctttgatg gtctgacccc gtataacgtt ggtcagtttt ttgcctatta cgaagcagca   1200

accgcattta tgggttatct gctggaaatt aatccgtttg atcagcctgg tgttgaactg   1260

ggcaaaaaaa tcacctttgc actgatgggt cgtgaaggct atacctatga aatcaaagaa   1320

cgcagcaaaa aagtgattat tgaataa                                       1347


<210> SEQ ID NO 13
<211> LENGTH: 216
<212> TYPE: PRT
<213> ORGANISM: Thermotoga naphthophila DSM 13996
<220> FEATURE:
<223> OTHER INFORMATION: Phosphatase

<400> SEQUENCE: 13

Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Pro Glu Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 14
<211> LENGTH: 651
<212> TYPE: DNA
<213> ORGANISM: Thermotoga naphthophila DSM 13996
<220> FEATURE:
<223> OTHER INFORMATION: coding for Phosphatase

<400> SEQUENCE: 14

atggaagcgg tgattttcga catggatgga gtgctcatgg acacagagcc tctctacttc     60
```

```
gaagcttaca gaagagtcgc ggaaagctat ggaaaacctt acacggagga tctccacagg    120

agaataatgg gagttcctga aagagaaggt cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccggg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651
```

<210> SEQ ID NO 15
<211> LENGTH: 216
<212> TYPE: PRT
<213> ORGANISM: Thermotoga naphthophila DSM 13996
<220> FEATURE:
<223> OTHER INFORMATION: Phosphatase-variant P46T

<400> SEQUENCE: 15

```
Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Thr Glu Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

<210> SEQ ID NO 16
<211> LENGTH: 650
<212> TYPE: DNA
<213> ORGANISM: Thermotoga naphthophila DSM 13996
<220> FEATURE:

<223> OTHER INFORMATION: coding for Phosphatase-variant P46T

<400> SEQUENCE: 16

```
atggaagcgg tgattttcga catggatgga gtgctcatgg acacagagcc tctctacttc     60
gaagcttaca gaagagtcgc ggaaagctat ggaaaacctt acacggagga tctccacagg    120
agaataatgg gagttactga aagagaaggt cttcccatcc tcatggaagc tctggagata    180
aaagattctc tggagaactt caaaaagagg gtccacgaag aaaaaaagcg cgttttctct    240
gagcttctca aggaaaatcc gggtgtaaga gaggcgctcg agttcgtaaa gagcaaaaga    300
ataaaactcg cgctcgcaac ctccacacca cagcgagaag cgctggagag attgagaaga    360
ctcgatctcg aaaagtactt cgacgtcatg gtgttcggtg atcaggtgaa gaacggaaag    420
cctgatccag agatatacct tctcgttctg gaaaggttga atgtggtccc agagaaggtt    480
gtggtcttcg aagactcaaa gagcggtgtt gaagccgcaa aagcgccgg catagaaaga    540
atctatggag tcgttcactc tttgaacgac ggtaaagcgc ttcttgaagc gggtgcggtt    600
gctctggtga aacccgagga aatcctgaac gttctcaaag aggttcttta               650
```

<210> SEQ ID NO 17
<211> LENGTH: 216
<212> TYPE: PRT
<213> ORGANISM: Thermotoga naphthophila DSM 13996
<220> FEATURE:
<223> OTHER INFORMATION: Phosphatase-variant P46TE47Y

<400> SEQUENCE: 17

```
Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

```
<210> SEQ ID NO 18
<211> LENGTH: 651
<212> TYPE: DNA
<213> ORGANISM: Thermotoga naphthophila DSM 13996
<220> FEATURE:
<223> OTHER INFORMATION: coding for Phosphatase-variant P46TE47Y

<400> SEQUENCE: 18

atggaagcgg tgattttcga catggatgga gtgctcatgg acacagagcc tctctacttc      60

gaagcttaca gaagagtcgc ggaaagctat ggaaaacctt acacggagga tctccacagg     120

agaataatgg gagttactta tagagaaggt cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420

cctgatccag agatatacct tctcgttctg gaaaggttga atgtggtccc agagaaggtt     480

gtggtcttcg aagactcaaa gagcggtgtt gaagccgcaa aagcgccgg catagaaaga      540

atctatggag tcgttcactc tttgaacgac ggtaaagcgc ttcttgaagc gggtgcggtt     600

gctctggtga aacccgagga aatcctgaac gttctcaaag aggttcttta a              651


<210> SEQ ID NO 19
<211> LENGTH: 216
<212> TYPE: PRT
<213> ORGANISM: Thermotoga naphthophila DSM 13996
<220> FEATURE:
<223> OTHER INFORMATION: Phosphatase-variant P46TE47YG50L

<400> SEQUENCE: 19

Met Glu Ala Val Ile Phe Asp Met Asp Gly Val Leu Met Asp Thr Glu
1               5                   10                  15

Pro Leu Tyr Phe Glu Ala Tyr Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205
```

Leu Asn Val Leu Lys Glu Val Leu
210 215

<210> SEQ ID NO 20
<211> LENGTH: 651
<212> TYPE: DNA
<213> ORGANISM: Thermotoga naphthophila DSM 13996
<220> FEATURE:
<223> OTHER INFORMATION: coding for Phosphatase-variant P46TE47YG50L

<400> SEQUENCE: 20
atggaagcgg tgattttcga catggatgga gtgctcatgg acacagagcc tctctacttc 60
gaagcttaca gaagagtcgc ggaaagctat ggaaaacctt acacggagga tctccacagg 120
agaataatgg gagttactta tagagaattg cttcccatcc tcatggaagc tctggagata 180
aaagattctc tggagaactt caaaaagagg gtccacgaag aaaaaaagcg cgttttctct 240
gagcttctca aggaaaatcc gggtgtaaga gaggcgctcg agttcgtaaa gagcaaaaga 300
ataaaactcg cgctcgcaac ctccacacca cagcgagaag cgctggagag attgagaaga 360
ctcgatctcg aaaagtactt cgacgtcatg gtgttcggtg atcaggtgaa gaacggaaag 420
cctgatccag agatatacct tctcgttctg gaaaggttga atgtggtccc agagaaggtt 480
gtggtcttcg aagactcaaa gagcggtgtt gaagccgcaa aaagcgccgg catagaaaga 540
atctatggag tcgttcactc tttgaacgac ggtaaagcgc ttcttgaagc gggtgcggtt 600
gctctggtga aacccgagga aatcctgaac gttctcaaag aggttcttta a 651

<210> SEQ ID NO 21
<211> LENGTH: 216
<212> TYPE: PRT
<213> ORGANISM: Thermotoga naphthophila DSM 13996
<220> FEATURE:
<223> OTHER INFORMATION: Phosphatase-variant P46TE47YG50I

<400> SEQUENCE: 21

Met Glu Ala Val Ile Phe Asp Met Asp Gly Val Leu Met Asp Thr Glu
1 5 10 15

Pro Leu Tyr Phe Glu Ala Tyr Arg Arg Val Ala Glu Ser Tyr Gly Lys
20 25 30

Pro Tyr Thr Glu Asp Leu His Arg Arg Ile Met Gly Val Thr Tyr Arg
35 40 45

Glu Leu Leu Pro Ile Leu Met Glu Ala Leu Glu Ile Lys Asp Ser Leu
50 55 60

Glu Asn Phe Lys Lys Arg Val His Glu Glu Lys Lys Arg Val Phe Ser
65 70 75 80

Glu Leu Leu Lys Glu Asn Pro Gly Val Arg Glu Ala Leu Glu Phe Val
85 90 95

Lys Ser Lys Arg Ile Lys Leu Ala Leu Ala Thr Ser Thr Pro Gln Arg
100 105 110

Glu Ala Leu Glu Arg Leu Arg Arg Leu Asp Leu Glu Lys Tyr Phe Asp
115 120 125

Val Met Val Phe Gly Asp Gln Val Lys Asn Gly Lys Pro Asp Pro Glu
130 135 140

Ile Tyr Leu Leu Val Leu Glu Arg Leu Asn Val Val Pro Glu Lys Val
145 150 155 160

Val Val Phe Glu Asp Ser Lys Ser Gly Val Glu Ala Ala Lys Ser Ala
165 170 175

```
Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 22
<211> LENGTH: 651
<212> TYPE: DNA
<213> ORGANISM: Thermotoga naphthophila DSM 13996
<220> FEATURE:
<223> OTHER INFORMATION: coding for Phosphatase-variant P46TE47YG50I

<400> SEQUENCE: 22

atggaagcgg tgattttcga catggatgga gtgctcatgg acacagagcc tctctacttc     60

gaagcttaca gaagagtcgc ggaaagctat ggaaaacctt acacggagga tctccacagg    120

agaataatgg gagttactta tagagaaatt cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aaagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651


<210> SEQ ID NO 23
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HP46TE47Y

<400> SEQUENCE: 23

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Gly Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
```

```
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 24
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23HP46TE47Y

<400> SEQUENCE: 24

atggaagcgg tgattttcga catggatgga gtgctcatgg acacagagcc tctctacttc     60

gaagctcata gaagagtcgc ggaaagctat ggaaaacctt acacggagga tctccacagg    120

agaataatgg gagttactta tagagaaggt cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aaagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651


<210> SEQ ID NO 25
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HP46TE47YG50L

<400> SEQUENCE: 25

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125
```

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215

<210> SEQ ID NO 26
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23HP46TE47YG50L

<400> SEQUENCE: 26
atggaagcgg tgattttcga catggatgga gtgctcatgg acacagagcc tctctacttc 60
gaagctcaca gaagagtcgc ggaaagctat ggaaaacctt acacggagga tctccacagg 120
agaataatgg gagttactta tagagaattg cttcccatcc tcatggaagc tctggagata 180
aaagattctc tggagaactt caaaaagagg gtccacgaag aaaaaaagcg cgttttctct 240
gagcttctca aggaaaatcc gggtgtaaga gaggcgctcg agttcgtaaa gagcaaaaga 300
ataaaactcg cgctcgcaac ctccacacca cagcgagaag cgctggagag attgagaaga 360
ctcgatctcg aaaagtactt cgacgtcatg gtgttcggtg atcaggtgaa gaacggaaag 420
cctgatccag agatatacct tctcgttctg gaaaggttga atgtggtccc agagaaggtt 480
gtggtcttcg aagactcaaa gagcggtgtt gaagccgcaa aaagcgccgg catagaaaga 540
atctatggag tcgttcactc tttgaacgac ggtaaagcgc ttcttgaagc gggtgcggtt 600
gctctggtga aacccgagga aatcctgaac gttctcaaag aggttcttta a 651

<210> SEQ ID NO 27
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HP46TE47YG50I

<400> SEQUENCE: 27

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Ile Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

```
Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

<210> SEQ ID NO 28
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23HP46TE47YG50I

<400> SEQUENCE: 28

```
atggaagcgg tgattttcga catggatgga gtgctcatgg acacagagcc tctctacttc      60

gaagctcaca gaagagtcgc ggaaagctat ggaaaacctt acacggagga tctccacagg     120

agaataatgg gagttactta tagagaaatt cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420

cctgatccag agatatacct tctcgttctg gaaaggttga atgtggtccc agagaaggtt     480

gtggtcttcg aagactcaaa gagcggtgtt gaagccgcaa aagcgccgg catagaaaga      540

atctatggag tcgttcactc tttgaacgac ggtaaagcgc ttcttgaagc gggtgcggtt     600

gctctggtga aacccgagga aatcctgaac gttctcaaag aggttcttta a              651
```

<210> SEQ ID NO 29
<211> LENGTH: 216
<212> TYPE: PRT
<213> ORGANISM: Thermotoga naphthophila DSM 13996
<220> FEATURE:
<223> OTHER INFORMATION: Phosphatase-variant Y23SP46TE47YG50L

<400> SEQUENCE: 29

```
Met Glu Ala Val Ile Phe Asp Met Asp Gly Val Leu Met Asp Thr Glu
1               5                   10                  15

Pro Leu Tyr Phe Glu Ala Ser Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
```

```
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 30
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23SP46TE47YG50L

<400> SEQUENCE: 30

atggaagcgg tgattttcga catggatgga gtgctcatgg acacagagcc tctctacttc     60

gaagcttcca gaagagtcgc ggaaagctat ggaaaacctt acacggagga tctccacagg    120

agaataatgg gagttactta tagagaattg cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651


<210> SEQ ID NO 31
<211> LENGTH: 216
<212> TYPE: PRT
<213> ORGANISM: Thermotoga naphthophila DSM 13996
<220> FEATURE:
<223> OTHER INFORMATION: Phosphatase-variant Y23SP46TE47YG50I

<400> SEQUENCE: 31

Met Glu Ala Val Ile Phe Asp Met Asp Gly Val Leu Met Asp Thr Glu
1               5                   10                  15

Pro Leu Tyr Phe Glu Ala Ser Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45
```

```
Glu Ile Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

<210> SEQ ID NO 32
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23SP46TE47YG50I

<400> SEQUENCE: 32

```
atggaagcgg tgattttcga catggatgga gtgctcatgg acacagagcc tctctacttc     60

gaagcttcca gaagagtcgc ggaaagctat ggaaaacctt acacggagga tctccacagg    120

agaataatgg gagttactta tagagaaatt cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccgg catagaaaga     540

atctatggag tcgttcactc tttgaacgac ggtaaagcgc ttcttgaagc gggtgcggtt    600

gctctggtga aacccgagga aatcctgaac gttctcaaag aggttcttta a             651
```

<210> SEQ ID NO 33
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HP46TE47TG50L

<400> SEQUENCE: 33

```
Met Glu Ala Val Ile Phe Asp Met Asp Gly Val Leu Met Asp Thr Glu
1               5                   10                  15
```

```
Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Thr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

<210> SEQ ID NO 34
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23HP46TE47TG50L

<400> SEQUENCE: 34

```
atggaagcgg tgattttcga catggatgga gtgctcatgg acacagagcc tctctacttc     60

gaagctcaca gaagagtcgc ggaaagctat ggaaaacctt acacggagga tctccacagg    120

agaataatgg gagttactac gagagaattg cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651
```

<210> SEQ ID NO 35
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HP46TE47FG50L

```
<400> SEQUENCE: 35

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 36
<211> LENGTH: 651
<212> TYPE: DNA
<213> ORGANISM: Thermotoga naphthophila DSM 13996
<220> FEATURE:
<223> OTHER INFORMATION: coding for Phosphatase-variant Y23HP46TE47FG50L

<400> SEQUENCE: 36

atggaagcgg tgattttcga catggatgga gtgctcatgg acacagagcc tctctacttc      60

gaagctcaca gaagagtcgc ggaaagctat ggaaaacctt acacggagga tctccacagg     120

agaataatgg gagttacttt tagagaattg cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420

cctgatccag agatatacct tctcgttctg gaaaggttga atgtggtccc agagaaggtt     480

gtggtcttcg aagactcaaa gagcggtgtt gaagccgcaa aagcgccgg catagaaaga     540

atctatggag tcgttcactc tttgaacgac ggtaaagcgc ttcttgaagc gggtgcggtt     600

gctctggtga aacccgagga aatcctgaac gttctcaaag aggttcttta a              651


<210> SEQ ID NO 37
<211> LENGTH: 216
```

```
<212> TYPE: PRT
<213> ORGANISM: Thermotoga naphthophila DSM 13996
<220> FEATURE:
<223> OTHER INFORMATION: Phosphatase-variant Y23HV45MP46TE47YG50L

<400> SEQUENCE: 37

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Met Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 38
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45MP46TE47YG50L

<400> SEQUENCE: 38

atggaagcgg tgattttcga catggatgga gtgctcatgg acacagagcc tctctacttc      60

gaagctcaca gaagagtcgc ggaaagctat ggaaaacctt acacggagga tctccacagg     120

agaataatgg gaatgactta tagagaattg cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420

cctgatccag agatatacct tctcgttctg gaaaggttga atgtggtccc agagaaggtt     480

gtggtcttcg aagactcaaa gagcggtgtt gaagccgcaa aagcgccgg catagaaaga     540

atctatggag tcgttcactc tttgaacgac ggtaaagcgc ttcttgaagc gggtgcggtt     600
```

```
gctctggtga aacccgagga aatcctgaac gttctcaaag aggttcttta a            651


<210> SEQ ID NO 39
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45QP46TE47YG50L

<400> SEQUENCE: 39

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Gln Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 40
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45QP46TE47YG50L

<400> SEQUENCE: 40

atggaagcgg tgattttcga catggatgga gtgctcatgg acacagagcc tctctacttc      60

gaagctcaca gaagagtcgc ggaaagctat ggaaaacctt acacggagga tctccacagg     120

agaataatgg gacagactta tagagaattg cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420
```

```
cctgatccag agatatacct tctcgttctg gaaaggttga atgtggtccc agagaaggtt    480

gtggtcttcg aagactcaaa gagcggtgtt gaagccgcaa aaagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651
```

```
<210> SEQ ID NO 41
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45RP46TE47YG50L

<400> SEQUENCE: 41

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Arg Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

```
<210> SEQ ID NO 42
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45RP46TE47YG50L

<400> SEQUENCE: 42

atggaagcgg tgattttcga catggatgga gtgctcatgg acacagagcc tctctacttc     60

gaagctcaca gaagagtcgc ggaaagctat ggaaaacctt acacggagga tctccacagg    120

agaataatgg gacgcactta tagagaattg cttcccatcc tcatggaagc tctggagata    180

aaagattctc tggagaactt caaaaagagg gtccacgaag aaaaaaagcg cgttttctct    240
```

```
gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651
```

<210> SEQ ID NO 43
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45RP46TE47TG50L

<400> SEQUENCE: 43

```
Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Arg Thr Thr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

<210> SEQ ID NO 44
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45RP46TE47TG50L

<400> SEQUENCE: 44

```
atggaagcgg tgattttcga catggatgga gtgctcatgg acacagagcc tctctacttc     60
```

```
gaagctcaca gaagagtcgc ggaaagctat ggaaaacctt acacggagga tctccacagg    120

agaataatgg gacgcactac cagagaattg cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aagcgccggg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651
```

```
<210> SEQ ID NO 45
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45RP46TE47FG50L

<400> SEQUENCE: 45

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 46
<211> LENGTH: 651
<212> TYPE: DNA
<213> ORGANISM: Thermotoga naphthophila DSM 13996
<220> FEATURE:
```

```
<223> OTHER INFORMATION: coding for Phosphatase-variant
      Y23HV45RP46TE47FG50L

<400> SEQUENCE: 46

atggaagcgg tgattttcga catggatgga gtgctcatgg acacagagcc tctctacttc     60

gaagctcaca gaagagtcgc ggaaagctat ggaaaacctt acacggagga tctccacagg    120

agaataatgg gacgcacttt cagagaattg cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aaagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651


<210> SEQ ID NO 47
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45MP46TE47FG50L

<400> SEQUENCE: 47

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Met Thr Phe Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190

Ala Leu Leu Glu Ala Gly Ala Val Ala Leu Val Lys Pro Glu Glu Ile
        195                 200                 205

Leu Asn Val Leu Lys Glu Val Leu
    210                 215
```

```
<210> SEQ ID NO 48
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45MP46TE47FG50L

<400> SEQUENCE: 48

atggaagcgg tgattttcga catggatgga gtgctcatgg acacagagcc tctctacttc     60

gaagctcaca gaagagtcgc ggaaagctat ggaaaacctt acacggagga tctccacagg    120

agaataatgg gaagtacttt cagagaattg cttcccatcc tcatggaagc tctggagata    180

aaagattctc tggagaactt caaaaagagg gtccacgaag aaaaaaagcg cgttttctct    240

gagcttctca aggaaaatcc gggtgtaaga gaggcgctcg agttcgtaaa gagcaaaaga    300

ataaaactcg cgctcgcaac ctccacacca cagcgagaag cgctggagag attgagaaga    360

ctcgatctcg aaaagtactt cgacgtcatg gtgttcggtg atcaggtgaa gaacggaaag    420

cctgatccag agatatacct tctcgttctg gaaaggttga atgtggtccc agagaaggtt    480

gtggtcttcg aagactcaaa gagcggtgtt gaagccgcaa aaagcgccgg catagaaaga    540

atctatggag tcgttcactc tttgaacgac ggtaaagcgc ttcttgaagc gggtgcggtt    600

gctctggtga aacccgagga aatcctgaac gttctcaaag aggttcttta a             651


<210> SEQ ID NO 49
<211> LENGTH: 216
<212> TYPE: PRT
<213> ORGANISM: Thermotoga naphthophila DSM 13996
<220> FEATURE:
<223> OTHER INFORMATION: Phosphatase-variant Y23HV45QP46TE47FG50L

<400> SEQUENCE: 49

Met Glu Ala Val Ile Phe Asp Met Asp Gly Val Leu Met Asp Thr Glu
1               5                   10                  15

Pro Leu Tyr Phe Glu Ala His Arg Arg Val Ala Glu Ser Tyr Gly Lys
            20                  25                  30

Pro Tyr Thr Glu Asp Leu His Arg Arg Ile Met Gly Val Thr Tyr Arg
        35                  40                  45

Glu Leu Leu Pro Ile Leu Met Glu Ala Leu Glu Ile Lys Asp Ser Leu
    50                  55                  60

Glu Asn Phe Lys Lys Arg Val His Glu Glu Lys Lys Arg Val Phe Ser
65                  70                  75                  80

Glu Leu Leu Lys Glu Asn Pro Gly Val Arg Glu Ala Leu Glu Phe Val
                85                  90                  95

Lys Ser Lys Arg Ile Lys Leu Ala Leu Ala Thr Ser Thr Pro Gln Arg
            100                 105                 110

Glu Ala Leu Glu Arg Leu Arg Arg Leu Asp Leu Glu Lys Tyr Phe Asp
        115                 120                 125

Val Met Val Phe Gly Asp Gln Val Lys Asn Gly Lys Pro Asp Pro Glu
    130                 135                 140

Ile Tyr Leu Leu Val Leu Glu Arg Leu Asn Val Val Pro Glu Lys Val
145                 150                 155                 160

Val Val Phe Glu Asp Ser Lys Ser Gly Val Glu Ala Ala Lys Ser Ala
                165                 170                 175

Gly Ile Glu Arg Ile Tyr Gly Val Val His Ser Leu Asn Asp Gly Lys
            180                 185                 190
```

```
Ala Leu Leu Glu Ala Gly Ala Val Ala Leu Val Lys Pro Glu Glu Ile
        195                 200                 205

Leu Asn Val Leu Lys Glu Val Leu
    210                 215


<210> SEQ ID NO 50
<211> LENGTH: 651
<212> TYPE: DNA
<213> ORGANISM: Thermotoga naphthophila DSM 13996
<220> FEATURE:
<223> OTHER INFORMATION: coding for Phosphatase-variant
      Y23HV45QP46TE47FG50L

<400> SEQUENCE: 50

atggaagcgg tgattttcga catggatgga gtgctcatgg acacagagcc tctctacttc      60

gaagctcaca gaagagtcgc ggaaagctat ggaaaacctt acacggagga tctccacagg     120

agaataatgg gacagacttt cagagaattg cttcccatcc tcatggaagc tctggagata     180

aaagattctc tggagaactt caaaaagagg gtccacgaag aaaaaaagcg cgttttctct     240

gagcttctca aggaaaatcc gggtgtaaga gaggcgctcg agttcgtaaa gagcaaaaga     300

ataaaactcg cgctcgcaac ctccacacca cagcgagaag cgctggagag attgagaaga     360

ctcgatctcg aaaagtactt cgacgtcatg gtgttcggtg atcaggtgaa gaacggaaag     420

cctgatccag agatatacct tctcgttctg gaaaggttga atgtggtccc agagaaggtt     480

gtggtcttcg aagactcaaa gagcggtgtt gaagccgcaa aaagcgccgg catagaaaga     540

atctatggag tcgttcactc tttgaacgac ggtaaagcgc ttcttgaagc gggtgcggtt     600

gctctggtga aacccgagga aatcctgaac gttctcaaag aggttcttta a             651


<210> SEQ ID NO 51
<211> LENGTH: 504
<212> TYPE: PRT
<213> ORGANISM: Bifidobacterium adolescentis
<220> FEATURE:
<223> OTHER INFORMATION: Sucrose Phosphorylase variant
      Q331ER393ND445PD446TQ460EE485H

<400> SEQUENCE: 51

Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160
```

```
Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Glu Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
    370                 375                 380

Gly Lys Asn Asp Met Glu Leu Leu Asn Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Pro Thr Asp Thr
        435                 440                 445

Ser Ile Ser Phe Thr Trp Arg Gly Glu Thr Ser Glu Ala Thr Leu Thr
    450                 455                 460

Phe Glu Pro Lys Arg Gly Leu Gly Val Asp Asn Thr Thr Pro Val Ala
465                 470                 475                 480

Met Leu Glu Trp His Asp Ser Ala Gly Asp His Arg Ser Asp Asp Leu
                485                 490                 495

Ile Ala Asn Pro Pro Val Val Ala
            500
```

<210> SEQ ID NO 52
<211> LENGTH: 1515
<212> TYPE: DNA
<213> ORGANISM: Bifidobacterium adolescentis
<220> FEATURE:
<223> OTHER INFORMATION: coding for Sucrose Phosphorylase variant
Q331ER393ND445PD446TQ460EE485H

<400> SEQUENCE: 52

```
atgaagaaca aagtgcagct gattacctat gcagatcgtt taggtgatgg caccattaaa     60
```

-continued

```
agcatgaccg atattctgcg tacccgtttt gatggtgtgt atgatggtgt tcatatcctg    120

ccgtttttta ccccgtttga tggcgcagat gcaggttttg atccgattga tcataccaaa    180

gtggatgaac gtttaggtag ctgggatgat gttgcagaac tgagcaaaac ccataacatt    240

atggttgatg ccattgtgaa tcacatgagc tgggaaagca aacagtttca ggatgttctg    300

gcaaaaggtg aagaaagcga atattatccg atgtttctga ccatgagcag cgtttttccg    360

aatggtgcaa ccgaagaaga tctggcaggt atttatcgtc cgcgtccggg tctgccgttt    420

acacattaca aatttgcagg taaaacccgt ctggtttggg ttagctttac accgcagcag    480

gttgatattg ataccgatag cgataaaggt tgggaatatc tgatgagcat ctttgatcag    540

atggcagcaa gccatgttag ctatattcgt ctggatgcag ttggttatgg tgcaaaagaa    600

gcaggcacca gctgttttat gaccccgaaa acctttaaac tgattagccg tctgcgtgaa    660

gaaggtgtta aacgcggtct ggaaattctg attgaagtgc acagctacta caagaaacag    720

gttgaaattg ccagcaaagt tgatcgcgtt tatgattttg cactgcctcc gctgctgctg    780

catgcactga gcaccggtca tgttgaaccg gttgcacatt ggacagatat tcgtccgaat    840

aatgcagtta ccgttctgga tacccatgat ggtattggtg ttattgatat tggtagcgat    900

cagctggatc gtagcctgaa aggtctggtt ccggatgaag atgttgataa tctggtgaat    960

accattcatg ccaatacaca tggtgaaagc gaggcagcaa ccggtgcagc agccagcaat   1020

ctggatctgt atcaggttaa tagcacctat tatagcgcac tgggttgtaa cgatcagcat   1080

tatattgcag cacgtgccgt tcagtttttt ctgcctggtg ttccgcaggt ttattatgtt   1140

ggtgcactgg caggcaaaaa tgatatggaa ctgctgaata aaaccaataa cggtcgtgat   1200

attaaccgcc attattacag caccgcagaa attgatgaaa atctgaaacg tccggttgtg   1260

aaagcactga atgcactggc caaatttcgc aatgaactgg atgcatttga tggcacattt   1320

agctatacca cccctactga taccagcatt tcatttacct ggcgtggtga aaccagcgag   1380

gcgaccctga cctttgaacc gaaacgtggt ctgggcgttg ataataccac accggtggca   1440

atgctggaat ggcacgatag tgccggtgat catcgtagtg atgatctgat tgcaaatccg   1500

cctgttgttg cataa                                                      1515
```

PRODUCTION OF FRUCTOSE FROM OLIGO-/ AND/OR POLYSACCHARIDES

The present invention relates to a method for converting at least one oligo- and/or polysaccharide into fructose, a composition for converting at least one oligo- and/or polysaccharide into fructose, and an aqueous composition comprising fructose. In addition, the present invention relates to a phosphatase and the use of the phosphatase in the conversion of at least one oligo- and/or polysaccharide.

Current industrial production processes of D-fructose are based in particular on a two-stage process. In the first step, a polysaccharide or oligosaccharide, for example starch, is cleaved by hydrolysis into monosaccharides. In the second step, an isomerization is carried out by which D-fructose is obtained with a yield (corresponding to a percentage) of about 42%. The subsequent work-up for the preparation of pure D-fructose is carried out by costly chromatographic purification techniques.

An alternative industrial process is the hydrolysis of sucrose with the enzyme invertase. An equimolar mixture of D-glucose and D-fructose is thereby obtained. To enrich the D-fructose this must be cleaned again by costly chromatographic procedures.

The industrial processes have a significant disadvantage, since only solutions of D-fructose are formed in which this makes up a maximum of 50% of the saccharides present in the solution. To obtain higher D-fructose solutions, either costly chromatographic purification must be done or expensive pure D-fructose must be added such as high fructose corn syrup with 55% fructose content (HFCS55).

An alternative process for the production of pure D-fructose using D-glucose as a substrate is known and described in detail in EP0028136B1 and AT513928B1. In this case, D-glucose is oxidized with a pyranose-2-oxidase to D-glucosone and is then reduced to D-fructose. The reduction can be carried out by chemical means, that is homogeneous or heterogeneous catalysis, or by using biocatalysts.

This process has not yet been technically realized. It has the disadvantage that the oxidation and the reduction must run separately from each other and so an additional process step is necessary. In addition, in the event that the reduction takes place chemically a high purity of the substrates is necessary and high pressures as well as temperatures are required, which can lead to an undesirable formation of by-products. In the case where the reduction is performed enzymatically, very high costs are incurred for the reducing agents and the unstable coenzymes used, such as NADH.

The known processes for the production of D-fructose have various disadvantages. For an efficient conversion of the substrates partly high pressures and temperatures are needed. Alternatively, only a maximum yield of 50% depending on the substrate can be achieved or the use of clean substrates to reduce by-products is necessary. The further concentration requires very clean process streams to ensure reuse of the chromatographic equipment.

There is a need for a method for converting oligo- and/or polysaccharides into D-fructose which overcomes above disadvantages such as the use of expensive cofactors or unfavorable equilibria requiring further chromatographic purification and concentration steps.

It is the object of the present invention to provide a method allowing D-fructose production with high yield in relation to the substrate and no or lesser side products. Besides, work-up should be simplified and the use of organic coenzymes should not be necessary.

The object is solved by the method for converting at least one oligo- and/or polysaccharide into fructose as claimed, a composition for converting at least one oligo- and/or polysaccharide into fructose as claimed, and an aqueous composition comprising fructose as claimed. In addition, the object is solved by the phosphatase as claimed and the use of the phosphatase in the conversion of at least one oligo- and/or polysaccharide as claimed.

In a first aspect the present invention relates to a method for converting at least one oligo- and/or polysaccharide into fructose comprising the steps of:

a) adding to a composition comprising water, phosphate and at least one oligo- and/or polysaccharide at least four enzymes, preferably at least five enzymes, and
b) subsequently enzymatically converting the at least one oligo- and/or polysaccharide to fructose in the presence of the at least four enzymes, preferably at least five enzymes, wherein in step a) at least one additional saccharide is added, whereby the at least one additional saccharide is selected from the group consisting of saccharides comprising 20 or less monosaccharide residues and/or combinations thereof, preferably saccharides comprising 17 or less monosaccharide residues and/or combinations thereof;

wherein in step a) the at least four enzymes, preferably at least five enzymes, are selected from the group consisting of transferases, phosphorylases, mutases, isomerases, hydrolases, phosphatases and combinations thereof; and wherein at least one enzyme in step a) is a phosphatase.

Further preferred embodiments are described in the dependent claims as well as in the description.

Reference to fructose in the context of the invention is to be understood as reference to D-fructose.

Oligosaccharides according to the invention are saccharides comprising at least two monosaccharide residues whereby these monosaccharide residues may be identical or different.

Under phosphatase any enzyme falling within the classification EC 3.1.3. is to be understood. Under transferase any enzyme falling within the classification EC 2.4. is to be understood. Under phosphorylase any enzyme falling within the classification EC 2.4.1. is to be understood. Under mutase any enzyme falling within the classification EC 5.4.2. is to be understood. Under isomerase any enzyme falling within the classification EC 5.3.1. is to be understood. Under hydrolase any enzyme falling within the classification EC 3.2. is to be understood.

As substrates according to the invention oligo- and polysaccharides can be used. The improved yield results from the sugar phosphates which can be prepared by cleavage of the saccharides and possibly fructose units already present in the saccharides.

Surprisingly, a production method for D-fructose was found, which works without high pressures and temperatures and better tolerates the presence of in-process contaminants. The choice of catalysts makes it possible to obtain a high yield of D-fructose in the process by forming intermediate sugar-phosphates. As a result, a higher proportion based on the substrates (saccharides) can be achieved than in the currently used industrial production methods and a workup is made superfluous. This eliminates costly cleaning procedures. Saccharides may be oligo- and/or polysaccharides.

Preferably the composition in step a) comprises equal or less than 35% of the at least one oligo- and/or polysaccharide on a dry weight basis. Preferably the composition comprises 0.5 to 35% of the at least one oligo- and/or polysaccharide on a dry weight basis.

Further preferred the oligo- and/or polysaccharide is selected from glucose based oligo- and/or polysaccharides, preferably from the group consisting of starch and derivatives thereof, hemicellulose and derivatives thereof, cellulose and derivatives thereof and/or combinations thereof.

The respective oligo- and/or polysaccharides may be obtained via starch production or by hydrolysis of biomass, for example in pulp production or in the processing of straw.

Preferably in step a) the at least one additional saccharide is selected from the group consisting of tetradecasaccharides, tridecasaccharides, dodecasaccharides, undecasaccharides, decasaccharides, nonasaccharides, octasaccharides, heptasaccharides, hexasaccharides, pentasaccharides, tetrasaccharides, trisaccharides, disaccharides and/or combinations thereof, more preferably tetrasaccharides, trisaccharides, disaccharides, and combinations thereof, even more preferably is selected from maltose, maltotriose, maltotetraose and combinations thereof.

Further preferred in step a) the at least one additional saccharide is maltodextrin. Maltodextrin is a saccharide consisting of D-glucose units, which are primarily linked with α-1,4-glycosidic bonds, connected in chains of variable length. Typically, maltodextrin is composed of a mixture of chains that vary from three to 17 glucose units long. Maltodextrins are classified by DE (dextrose equivalent) and have a DE between 3 and 20. The higher the DE value the shorter the glucose chains.

Further preferred the at least one additional saccharide has at least partially the same glycosidic linkage as the at least one oligo- and/or polysaccharide.

Preferably the phosphatase comprises an amino acid sequence that is at least 90%, preferably at least 95%, more preferably at least 97% and even more preferably at least 98.5% identical with the sequence according to SEQ ID NO: 13.

In a preferred embodiment the phosphatase comprises an amino acid sequence that is at least 98%, preferably at least 98.5%, more preferably at least 99% and even more preferably at least 99.5% identical with the sequence according to SEQ ID NO: 41.

According to a preferred embodiment the phosphatase is selected from the group of phosphatases having an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

Furthermore, in step a) preferably at least six enzymes are added to the composition.

Preferably the at least four enzymes, more preferably five enzymes and even more preferably six enzymes are selected from the group consisting of phosphatase, transferase, phosphorylase, mutase, isomerase and/or hydrolase.

Preferably in step a) at least one transferase, preferably a glycosyltransferase, more preferably a glucanotransferase, even more preferably an alpha-glucanotransferase is added; and/or preferably in step a) at least one phosphorylase, preferably a glucanphosphorylase is added; and/or preferably in step a) at least one mutase, preferably a phosphoglucomutase is added; and/or preferably in step a) at least one isomerase, preferably a phosphoglucoisomerase is added; and/or preferably in step a) at least one hydrolase, preferably a glucanohydrolase, more preferably Pullulanase is added.

According to a preferred embodiment of the method for converting at least one oligo- and/or polysaccharide into fructose in step a) the at least one additional saccharide is selected from the group consisting of tetrasaccharides, trisaccharides, disaccharides, and combinations thereof, more preferably is selected from maltose, maltotriose, maltotetraose and combinations thereof; and/or the composition in step a) comprises equal or less than 35% of the at least one oligo- and/or polysaccharide on a dry weight basis, preferably the composition comprises 0.5% to 35% of the at least one oligo- and/or polysaccharide on a dry weight basis; and/or the at least one oligo- and/or polysaccharide is selected from glucose based oligo- and/or polysaccharides, preferably from the group consisting of starch and derivatives thereof, hemicellulose and derivatives thereof, cellulose and derivatives thereof and/or combinations thereof; and/or in step a) at least six enzymes are added to the composition; and/or the at least one additional saccharide has at least partially the same glycosidic linkage as the at least one oligo- and/or polysaccharide.

Preferably in step b) saccharide phosphates are intermediary produced.

Further preferred in step b) the enzymatic conversion is a one-pot reaction.

According to a preferred embodiment in step b) saccharide phosphates are intermediary produced and the enzymatic conversion is a one-pot reaction.

The inventive method allows the conversion of oligo- and polysaccharides to D-fructose by several catalytic steps. This results in intermediates in the form of sugar phosphates, which are ultimately cleaved to D-fructose and phosphate.

Preferably the oligo- and/or polysaccharide added in step a) comprises a plurality of glucose units, more preferably D-glucose units. Even more preferred the oligo- and/or polysaccharide added in step a) consists of a plurality of glucose units, more preferably D-glucose units.

In the inventive method according to one embodiment is an enzymatic process a reaction sequence is applied, enabling the cleavage of individual D-glucose molecules in the form of D-glucose-1-phosphate. Subsequently, these released D-glucose-1-phosphate molecules are converted via further sugar-phosphate intermediates into D-fructose-6-phosphate. D-fructose-6-phosphate is subsequently split, and D-fructose and phosphate are obtained.

Reaction steps during this conversion comprise the following steps: a saccharide molecule is enzymatically D-glucose-1-phosphate cleaved, and D-glucose-1-phosphate is enzymatically converted to D-glucose-6-phosphate, and D-glucose-6-phosphate is enzymatically converted to D-fructose-6-phosphate, and D-fructose-6-phosphate is enzymatically cleaved into D-fructose and phosphate.

Phosphate is used only in small catalytic amounts to intermediately form sugar phosphates such as for example D-glucose-1-phosphate, D-glucose-6-phosphate, D-fructose-6-phosphate. In the initial step phosphate is added to a D-glucose unit containing mixture and in the final step phosphate is cleaved off and made available again for the initial step.

This method of the present invention provides an enzymatic alternative to the production of D-fructose as known in the art and it greatly simplifies the need to separate and purify residual intermediates. Thus, the present invention represents a significant improvement in the production of D-fructose from saccharides over currently used techniques. In contrast to existing methods, the biocatalyst system used achieves enhanced enrichment of the product D-fructose.

The method is basically suitable for the use of oligo- and polysaccharides.

Preferably from cellobiose, maltose or starch, a hydrolyzate rich in D-fructose can be produced. In this case, the initial step is carried out using cellobiose phosphorylase, maltose phosphorylase or starch phosphorylase followed by several catalytic steps. The method is particularly useful in the use of sucrose as a substrate, which can be obtained from sugar beet or cane. In this case, the initial step is carried out using sucrosephosphorylase. In this particular case, D-fructose with yields of >53% (based on the mass) or >1 mol D-fructose per mol of sucrose are obtained.

The method of the present invention can be carried out in various solvent systems. Preferably it is carried out in aqueous solvent systems.

It is also possible to supplement the aqueous system by a buffer system. Suitable buffers (systems) are known and include conventional buffers (systems), for example, acetate, potassium phosphate, Tris-HCl, glycylglycine and glycine buffers, or mixtures of these.

Preferably, a buffer used in a method of the present invention has a pH of 3 to 12, preferably 4 to 12, more preferably 4 to 11. For optimum activity of the biocatalysts ions, e.g. $Mg^{2+}$, to be added. The use of stabilizers, glycerol etc. may allow longer use of biocatalysts.

In the method of the present invention, phosphate is needed. In order to ensure a sufficient amount of phosphate in the process, external addition in the form of phosphoric acid, salts of phosphoric acid, polyphosphate or combinations thereof is necessary.

Preferably the inventive method is carried out at suitable temperatures, e.g. may depend on the enzymes used. Suitable temperatures include 10 to 100° C., preferably 10 to 90° C., more preferably 20 to 90° C., even more preferably 20 to 80° C.

Preferably the temperature in step b) is between 10-100° C., more preferably between 20-90° C. and even more preferably between 20-80° C.

Further preferred the pH of the composition is between 3 to 12 and more preferably 4 to 10. An advantage of the inventive method is that it performs all the catalytic steps in the same reaction batch without the need to isolate intermediates. The method can be operated either batchwise or continuously. In this case, either all the enzymes involved can be added simultaneously or only a portion of the enzymes is added, e.g. the enzyme(s) can be added during step b) and, with temporal or local delay, another part of the enzymes can be added later.

Before the addition of the second part of the enzymes, the enzymes already present in the reaction mixture can be removed, for example, physically (filtration or via immobilization) or inactivated. The latter can be done by a short-term increase in temperature to, for example, 80° C. for 10 min. Alternatively, the reaction solution can also run through the reaction mixture for increased conversion and yields several times.

The cleavage of saccharides into D-glucose-1-phosphate in the inventive method is enzymatic, namely by enzymatic catalysis, and may be carried out according to a known method. The cleavage is preferably carried out by catalysis with a phosphorylase.

Preferably at least 50% of the saccharides present in the composition of step a) are converted to fructose after 24 h of enzymatic conversion.

Also preferably at least 70% of the saccharides present in the composition of step a) are converted to fructose after 48 h of enzymatic conversion.

The inventive method allows further an improved handling of high concentrated oligo- and/or polysaccharides such as swollen starch. It is for example possible to run the inventive method with a starting concentration of 35% dry substance starch.

Preferably step b) is performed for at least 24 h at room temperature (25° C.).

In another aspect the present invention relates to a method for converting at least one oligo- and/or polysaccharide into fructose comprising the steps of: a) adding to a composition comprising water, phosphate and at least one oligo- and/or polysaccharide at least one enzyme, and b) subsequently enzymatically converting the at least one oligo- and/or polysaccharide to fructose in the presence of the at least one enzyme, wherein in step a) at least one additional saccharide is added, whereby the at least one additional saccharide is selected from the group consisting of saccharides comprising 20 or less monosaccharide residues and/or combinations thereof, preferably 17 or less monosaccharide residues and/or combinations thereof.

All remarks with respect to the method for converting at least one oligo- and/or polysaccharide into fructose, in particular with respect to enzymes and the oligo- and/or polysaccharides as mentioned hereinbefore also apply to this method where applicable.

Preferably the at least one enzyme in step a) is a phosphatase.

Furthermore, in step a) preferably at least four enzymes, more preferably at least five enzymes, and even more preferably at least six enzymes are added to the composition.

In a second aspect the invention relates to a composition for converting at least one oligo- and/or polysaccharide into fructose comprising water;

phosphate;

at least four enzymes, preferably at least five enzymes, wherein at least one enzyme is a phosphatase;

at least one oligo- and/or polysaccharide;

wherein the at least four enzymes, preferably at least five enzymes, are selected from the group consisting of transferases, phosphorylases, mutases, isomerase, hydrolases, phosphatases and combinations thereof; and wherein the composition further comprises at least one additional saccharide, whereby the at least one additional saccharide is selected from the group consisting of saccharides comprising 20 or less monosaccharide residues and/or combinations thereof, preferably 17 or less monosaccharide residues and/or combinations thereof.

All remarks with respect to the method for converting at least one oligo- and/or polysaccharide into fructose, in particular with respect to enzymes and the oligo- and/or polysaccharides as mentioned hereinbefore also apply to the composition for converting at least one oligo- and/or polysaccharide into fructose where applicable.

According to a preferred embodiment the phosphatase comprises an amino acid sequence that is at least 90%, preferably at least 95%, more preferably at least 97% and even more preferably at least 98.5% identical with the sequence according to SEQ ID NO: 13.

According to another preferred embodiment the phosphatase comprises an amino acid sequence that is at least 98%, preferably at least 98.5%, more preferably at least 99% and even more preferably at least 99.5% identical with the sequence according to SEQ ID NO: 41. According to a preferred embodiment the phosphatase is selected from the group of phosphatases having an amino acid sequence according to SEQ ID NO: 15, SEQ ID NO: 17, SEQ ID NO:

19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

Preferably the at least four enzymes, more preferably five enzymes and even more preferably six enzymes are selected from the group consisting of phosphatase, transferase, phosphorylase, mutase, isomerase and/or hydrolase.

According to a preferred embodiment the composition comprises a transferase, preferably a glycosyltransferase, more preferably a glucanotransferase, even more preferably an alpha-glucanotransferase; and/or the composition further comprises a phosphorylase, preferably a glucanphosphorylase is added; and/or the composition comprises a mutase, preferably a phosphoglucomutase; and/or the composition comprises an isomerase, preferably a phosphoglucoisomerase; and/or the composition comprises a hydrolase, preferably a glucanohydrolase, more preferably Pullulanase.

In another aspect the invention relates to a composition for converting at least one oligo- and/or polysaccharide into fructose comprising water; phosphate; at least five enzymes, wherein at least one enzyme is a phosphatase; at least one oligo- and/or polysaccharide; wherein the phosphatase comprises an amino acid sequence that is at least 90%, preferably at least 95%, more preferably at least 97% and even more preferably at least 98.5% identical with the sequence according to SEQ ID NO: 13.

All remarks with respect to the method for converting at least one oligo- and/or polysaccharide into fructose, in particular with respect to enzymes and the oligo- and/or polysaccharides and the composition for converting at least one oligo- and/or polysaccharide into fructose as mentioned hereinbefore also apply to this aspect where applicable.

Preferably the at least five enzymes are selected from the group consisting of phosphatase, transferase, phosphorylase, mutase, isomerase and/or hydrolase.

In a third aspect the invention relates to an aqueous composition comprising

- at least 50% fructose on a dry weight basis;
- 0.001 to 25% of glucose, preferably 0.005 to 20% of glucose on a dry weight basis;
- 0.01 to 22% of phosphate, preferably 0.05 to 20% of phosphate on a dry weight basis; and
- 0.001 to 2% of at least four enzymes, preferably at least five enzymes, preferably 0.005 to 1% of at least four enzymes, preferably at least five enzymes, on a dry weight basis, wherein the at least four enzymes, preferably at least five enzymes, are selected from the group consisting of transferases, phosphorylases, mutases, isomerase, hydrolases, phosphatases and combinations thereof; and wherein at least one enzyme is a phosphatase.

All remarks with respect to the method for converting at least one oligo- and/or polysaccharide into fructose, in particular with respect in particular with respect to enzymes and the oligo- and/or polysaccharides as mentioned hereinbefore also apply to the aqueous composition where applicable.

According to a preferred embodiment the phosphatase comprises an amino acid sequence that is at least 90%, preferably at least 95%, more preferably at least 97% and even more preferably at least 98.5% identical with the sequence according to SEQ ID NO: 13.

According to another preferred embodiment the phosphatase comprises an amino acid sequence that is at least 98%, preferably at least 98.5%, more preferably at least 99% and even more preferably at least 99.5% identical with the sequence according to SEQ ID NO: 41. According to a preferred embodiment the phosphatase is selected from the group of phosphatases having an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

Preferably the at least four enzymes, more preferably five enzymes and even more preferably six enzymes are selected from the group consisting of phosphatase, transferase, phosphorylase, mutase, isomerase and/or hydrolase.

According to a preferred embodiment the composition comprises a transferase, preferably a glycosyltransferase, more preferably a glucanotransferase, even more preferably an alpha-glucanotransferase; and/or the composition further comprises a phosphorylase, preferably a glucanphosphorylase is added; and/or the composition comprises a mutase, preferably a phosphoglucomutase; and/or the composition comprises an isomerase, preferably a phosphoglucoisomerase; and/or the composition comprises a hydrolase, preferably a glucanohydrolase, more preferably pullulanase.

In a fourth aspect the invention relates to an aqueous composition comprising

- at least 50% fructose on a dry weight basis;
- 0.001 to 25% of glucose, preferably 0.005 to 20% of glucose on a dry weight basis;
- 0.01 to 22% of phosphate, preferably 0.05 to 20% of phosphate on a dry weight basis; and
- 0.001 to 2% of at least four enzymes, preferably at least five enzymes, preferably 0.005 to 1% of at least four enzymes, preferably at least five enzymes, on a dry weight basis, wherein the at least four enzymes, preferably at least five enzymes, are selected from the group consisting of transferases, phosphorylases, mutases, isomerase, hydrolases, phosphatases and combinations thereof; and wherein at least one enzyme is a phosphatase, which is obtainable by the inventive method described above.

All remarks with respect to the method for converting at least one oligo- and/or polysaccharide into fructose, in particular with respect to enzymes and the oligo- and/or polysaccharides as mentioned hereinbefore also apply to the aqueous composition obtainable by the inventive method where applicable.

According to a preferred embodiment the phosphatase comprises an amino acid sequence that is at least 90%, preferably at least 95%, more preferably at least 97% and even more preferably at least 98.5% identical with the sequence according to SEQ ID NO: 13.

According to another preferred embodiment wherein the phosphatase comprises an amino acid sequence that is at least 98%, preferably at least 98.5%, more preferably at least 99% and even more preferably at least 99.5% identical with the sequence according to SEQ ID NO: 41.

According to a preferred embodiment the phosphatase is selected from the group of phosphatases having an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

Preferably the at least four enzymes, more preferably five enzymes and even more preferably six enzymes are selected from the group consisting of phosphatase, transferase, phosphorylase, mutase, isomerase and/or hydrolase.

According to a preferred embodiment the composition comprises a transferase, preferably a glycosyltransferase, more preferably a glucanotransferase, even more preferably an alpha-glucanotransferase; and/or the composition further comprises a phosphorylase, preferably a glucanphosphorylase is added; and/or the composition comprises a mutase, preferably a phosphoglucomutase; and/or the composition comprises an isomerase, preferably a phosphoglucoisomerase; and/or the composition comprises a hydrolase, preferably a glucanohydrolase, more preferably pullulanase.

In another aspect the invention relates to an aqueous composition comprising at least 50% fructose on a dry weight basis; less than 25% of glucose, preferably less than 20% of glucose, on a dry weight basis; less than 22% of phosphate, preferably less than 20% of phosphate, on a dry weight basis; and less than 2% of at least four enzymes, preferably less than 1% of at least four enzymes, on a dry weight basis, wherein one enzyme is a phosphatase.

All remarks with respect to the method for converting at least one oligo- and/or polysaccharide into fructose, in particular with respect to enzymes and the oligo- and/or polysaccharides as mentioned hereinbefore also apply to the aqueous composition where applicable.

According to a preferred embodiment the phosphatase comprises an amino acid sequence that is at least 90%, preferably at least 95%, more preferably at least 97% and even more preferably at least 98.5% identical with the sequence according to SEQ ID NO: 13.

According to a preferred embodiment the phosphatase is selected from the group of phosphatases having an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

According to a preferred embodiment the composition comprises a transferase, preferably a glycosyltransferase, more preferably a glucanotransferase, even more preferably an alpha-glucanotransferase; and/or the composition further comprises a phosphorylase, preferably a glucanphosphorylase is added; and/or the composition comprises a mutase, preferably a phosphoglucomutase; and/or the composition comprises an isomerase, preferably a phosphoglucoisomerase; and/or the composition comprises a hydrolase, preferably a glucanohydrolase, more preferably pullulanase.

In another aspect the invention relates to an aqueous composition comprising at least 50% fructose on a dry weight basis; less than 25% of glucose, preferably less than 20% of glucose, on a dry weight basis; less than 22% of phosphate, preferably less than 20% of phosphate, on a dry weight basis; and less than 2% of at least four enzymes, preferably less than 1% of at least four enzymes, on a dry weight basis, wherein one enzyme is a phosphatase, which is obtainable by the inventive method described above.

All remarks with respect to the method for converting at least one oligo- and/or polysaccharide into fructose, in particular with respect to enzymes and the oligo- and/or polysaccharides as mentioned hereinbefore also apply to the aqueous composition obtainable by the inventive method where applicable.

According to a preferred embodiment the phosphatase comprises an amino acid sequence that is at least 90%, preferably at least 95%, more preferably at least 97% and even more preferably at least 98.5% identical with the sequence according to SEQ ID NO: 13.

According to a preferred embodiment the phosphatase is selected from the group of phosphatases having an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

According to a preferred embodiment the composition comprises a transferase, preferably a glycosyltransferase, more preferably a glucanotransferase, even more preferably an alpha-glucanotransferase; and/or the composition further comprises a phosphorylase, preferably a glucanphosphorylase is added; and/or the composition comprises a mutase, preferably a phosphoglucomutase; and/or the composition comprises an isomerase, preferably a phosphoglucoisomerase; and/or the composition comprises a hydrolase, preferably a glucanohydrolase, more preferably pullulanase.

In another aspect the invention relates to fructose obtainable by the inventive method described above.

All remarks with respect to the method for converting at least one oligo- and/or polysaccharide into fructose, in particular with respect in particular with respect to enzymes and the oligo- and/or polysaccharides as mentioned hereinbefore also apply to the fructose obtainable by the inventive method where applicable.

In a fifth aspect the invention relates to a phosphatase comprising an amino acid sequence that is at least 98%, preferably at least 98.5%, more preferably at least 99% and even more preferably at least 99.5% identical with the sequence according to SEQ ID NO: 41.

All remarks with respect to the method for converting at least one oligo- and/or polysaccharide into fructose, in particular with respect in particular with respect to enzymes and the oligo- and/or polysaccharides as mentioned hereinbefore also apply to the phosphatase where applicable.

Preferably the phosphatase has an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49. Those phosphatases provide a higher yield in D-fructose. The inventive phosphatases provide an improved selectivity with respect to fructose-6-phosphate. Due to their higher activity it is possible to lower the amount of enzymes to be applied. Therefore, these phosphatases are particularly suited for industrial processes.

In another aspect the invention relates to a phosphatase comprising an amino acid sequence that is at least 90%, preferably at least 95%, more preferably at least 97% and even more preferably at least 98.5% identical with the sequence according to SEQ ID NO: 13.

Preferably the phosphatase has an amino acid sequence according to SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, or SEQ ID NO: 49.

All remarks with respect to the method for converting at least one oligo- and/or polysaccharide into fructose, in particular with respect in particular with respect to enzymes and the oligo- and/or polysaccharides as mentioned hereinbefore also apply to the phosphatase where applicable.

In an sixth aspect the invention relates to the use of an inventive phosphatase in the conversion of at least one oligo- and/or polysaccharide into fructose.

All remarks with respect to the method for converting at least one oligo- and/or polysaccharide into fructose, in particular with respect in particular with respect to enzymes and the oligo- and/or polysaccharides as mentioned hereinbefore also apply to the use of the inventive phosphatase where applicable.

Figure 1:
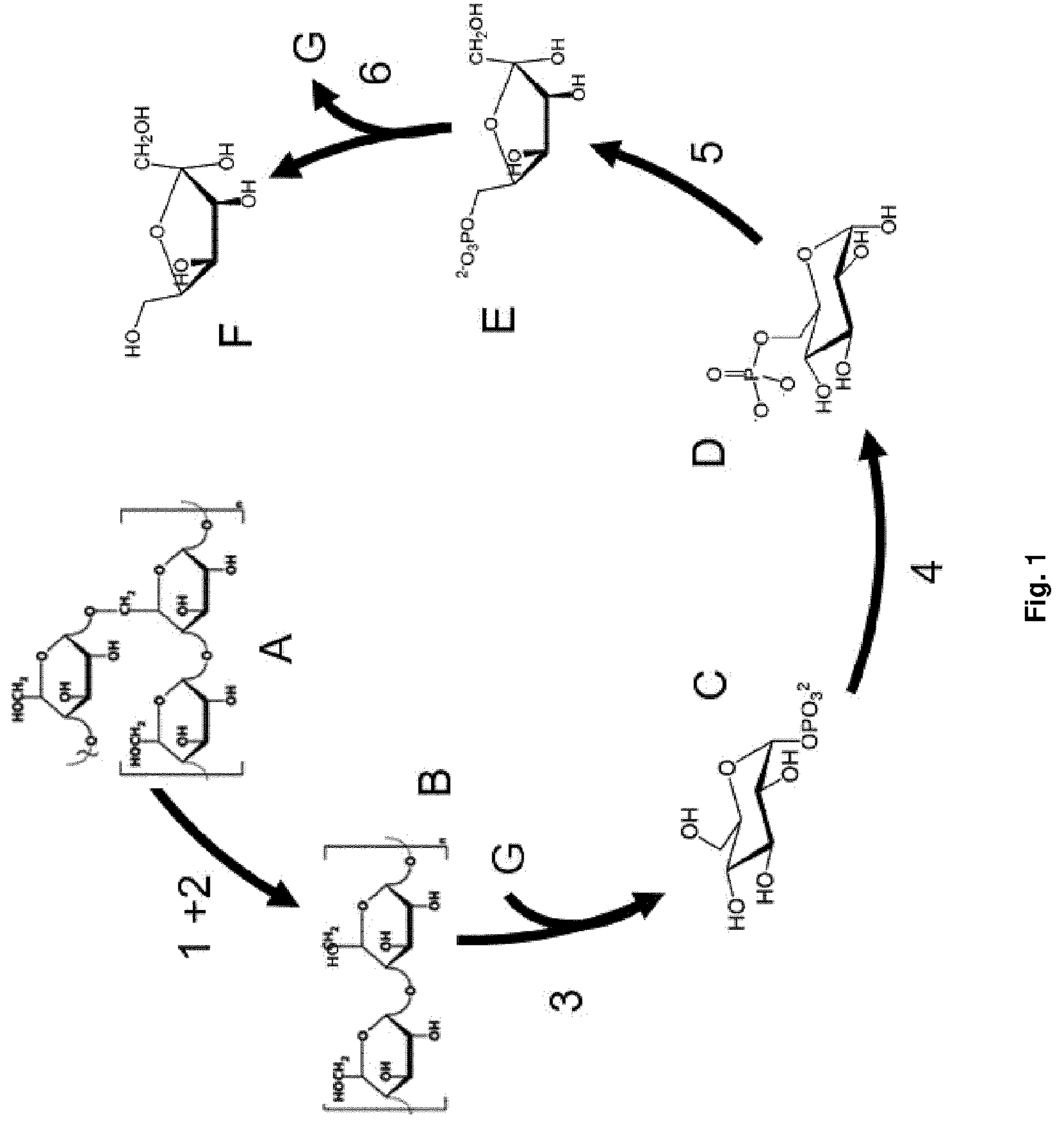
FIG. 1 Schematic representation of the inventive process starting with starch and resulting in fructose.

In the following the abbreviations and the enzymes used in the figures and/or tables are explained:

1 Pullulanase
2 α-Glucanotransferase
3 Glucan phosphorylase
4 Phosphoglucomutase
5 Phosphoglucoisomerase
6 Phosphatase
A Starch
B Amylose
B-A Amylose minus 1 Glucose unit
C Glucose-1-Phosphate (G1P)
D Glucose-6-Phosphate (G6P)
E Fructose-6-Phosphate (F6P)
F Fructose
G Phosphate
H Amylopectin
WT Wildtype; SEQ ID NO: 13;
T Phosphatase variant with an amino acid exchange at position 46 from proline to threonine (P46T); SEQ ID NO. 15;
TY Phosphatase variant with an amino acid exchange at position 46 from proline to threonine and an additional at position 47 from glutamate to tyrosine (P46TE47Y); SEQ ID NO. 17;
TYL Phosphatase variant with an amino acid exchange at position 46 from proline to threonine and at position 47 from glutamate to tyrosine and at position 50 from glycine to leucine (P46TE47YG50L); SEQ ID NO. 19;
HTY Phosphatase variant with an amino acid exchange at position 46 from proline to threonine and at position 47 from glutamate to tyrosine and at position 23 from tyrosine to histidine (Y23HP46TE47Y); SEQ ID NO. 23;
TYI Phosphatase variant with an amino acid exchange at position 46 from proline to threonine and at position 47 from glutamate to tyrosine and at position 50 from glycine to isoleucine (P46TE47YG50I); SEQ ID NO. 21;
HTYL Phosphatase variant with an amino acid exchange at position 46 from proline to threonine and at position 47 from glutamate to tyrosine and at position 50 from glycine to leucine and at position 23 from tyrosine to histidine (Y23HP46TE47YG50L); SEQ ID NO. 25;
HTYI Phosphatase variant with an amino acid exchange at position 46 from proline to threonine and at position 47 from glutamate to tyrosine and at position 50 from glycine to isoleucine and at position 23 from tyrosine to histidine (Y23HP46TE47YG50I); SEQ ID NO. 27;
STYL Phosphatase variant with an amino acid exchange at position 46 from proline to threonine and at position 47 from glutamate to tyrosine and at position 50 from glycine to leucine and at position 23 from tyrosine to serine (Y23SP46TE47YG50L); SEQ ID NO. 29;
STYI Phosphatase variant with an amino acid exchange at position 46 from proline to threonine and at position 47 from glutamate to tyrosine and at position 50 from glycine to isoleucine and at position 23 from tyrosine to serine (Y23SP46TE47YG50I); SEQ ID NO. 31;
Y47T/HTTL Phosphatase variant with an amino acid exchange at position 46 from proline to threonine and at position 47 from glutamate to threonine and at position 50 from glycine to leucine and at position 23 from tyrosine to histidine (Y23HP46TE47TG50L); SEQ ID NO. 33;

Y47F/HTFL Phosphatase variant with an amino acid exchange at position 46 from proline to threonine and at position 47 from glutamate to phenylalanine and at position 50 from glycine to leucine and at position 23 from tyrosine to histidine (Y23HP46TE47FG50L); SEQ ID NO. 35;

V45M Phosphatase variant with an amino acid exchange at position 46 from proline to threonine and at position 47 from glutamate to tyrosine and at position 50 from glycine to leucine and at position 23 from tyrosine to histidine and at position 45 from valine to methionine (Y23HV45MP46TE47YG50L); SEQ ID NO. 37;

V45Q Phosphatase variant with an amino acid exchange at position 46 from proline to threonine and at position 47 from glutamate to tyrosine and at position 50 from glycine to leucine and at position 23 from tyrosine to histidine and at position 45 from valine to glutamine (Y23HV45QP46TE47YG50L); SEQ ID NO. 39;

V45R Phosphatase variant with an amino acid exchange at position 46 from proline to threonine and at position 47 from glutamate to tyrosine and at position 50 from glycine to leucine and at position 23 from tyrosine to histidine and at position 45 from valine to arginine (Y23HV45RP46TE47YG50L); SEQ ID NO. 41;

HTTLV45R Phosphatase variant with an amino acid exchange at position 46 from proline to threonine and at position 47 from glutamate to threonine and at position 50 from glycine to leucine and at position 23 from tyrosine to histidine and at position 45 from valine to arginine (Y23HV45RP46TE47TG50L); SEQ ID NO. 43;

HTFLV45R Phosphatase variant with an amino acid exchange at position 46 from proline to threonine and at position 47 from glutamate to phenylalanine and at position 50 from glycine to leucine and at position 23 from tyrosine to histidine and at position 45 from valine to arginine (Y23HV45RP46TE47FG50L); SEQ ID NO. 45;

HTFLV45M Phosphatase variant with an amino acid exchange at position 46 from proline to threonine and at position 47 from glutamate to phenylalanine and at position 50 from glycine to leucine and at position 23 from tyrosine to histidine and at position 45 from valine to methionine (Y23HV45MP46TE47FG50L); SEQ ID NO. 47;

HTFLV45Q Phosphatase variant with an amino acid exchange at position 46 from proline to threonine and at position 47 from glutamate to phenylalanine and at position 50 from glycine to leucine and at position 23 from tyrosine to histidine and at position 45 from valine to glutamine (Y23HV45QP46TE47FG50L); SEQ ID NO. 49.

FIG. 1 shows the schematic representation of the inventive process starting with starch (A—mixture of amylose and amylopectin) which is converted to amylose (B) by use of pullulanase (1) and α-Glucanotransferase (2), the following step is catalyzed by a phosphorylase (glucan phosphorylase (3)) using inorganic phosphate (G) to cleave an α-1,4 linkage between the terminal glucose residue and the rest of the polymer to release glucose-1-phosphate (C), C is converted by the action of a phosphoglucomutase (4) to glucose-6-phosphate (D), glucose-6-phosphate is converted to fructose-6-phosphate (E) using a phosphoglucoisomerase (5) in the last step fructose-6-phosphate is cleaved into fructose (F) and phosphate (G) by the action of a phosphatase (6).

Figures 2, 3, 4:
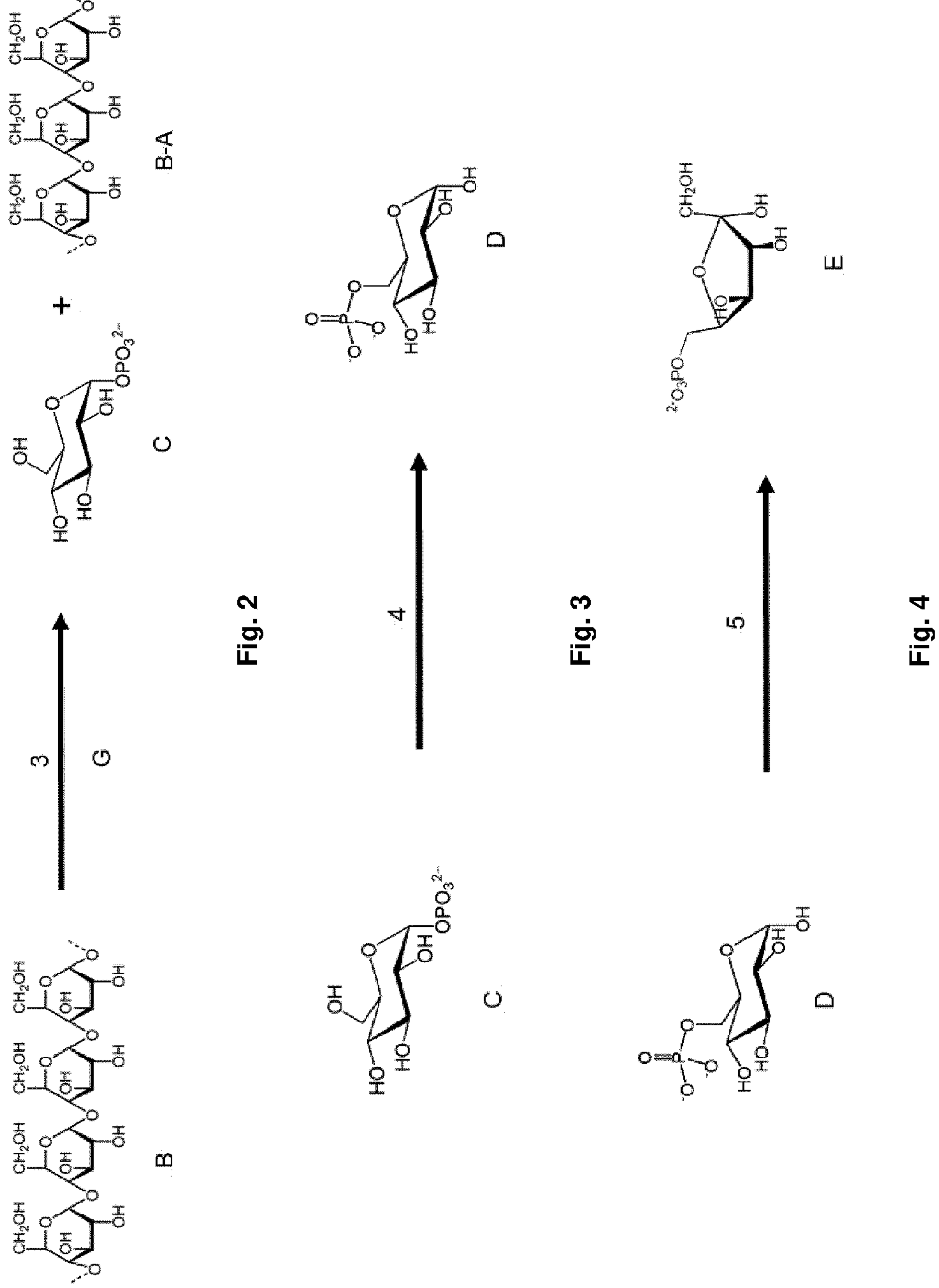
FIG. 2 intermediate step of the process shown in FIG. 1; glucan phosphorylase (3) using inorganic phosphate (G) to cleave an α-1,4 linkage between the terminal glucose residue and the rest of the polymer (B-A) to release glucose-1-phosphate (C)
FIG. 3 intermediate step of the process shown in FIG. 1; glucose-1-phosphate (C) is converted by the action of a phosphoglucomutase (4) to glucose-6-phosphate (D)
FIG. 4 intermediate step of the process shown in FIG. 1; glucose-6-phosphate is converted to fructose-6-phosphate (E) using a phosphoglucoisomerase (5)
Figures 5, 6, 7:
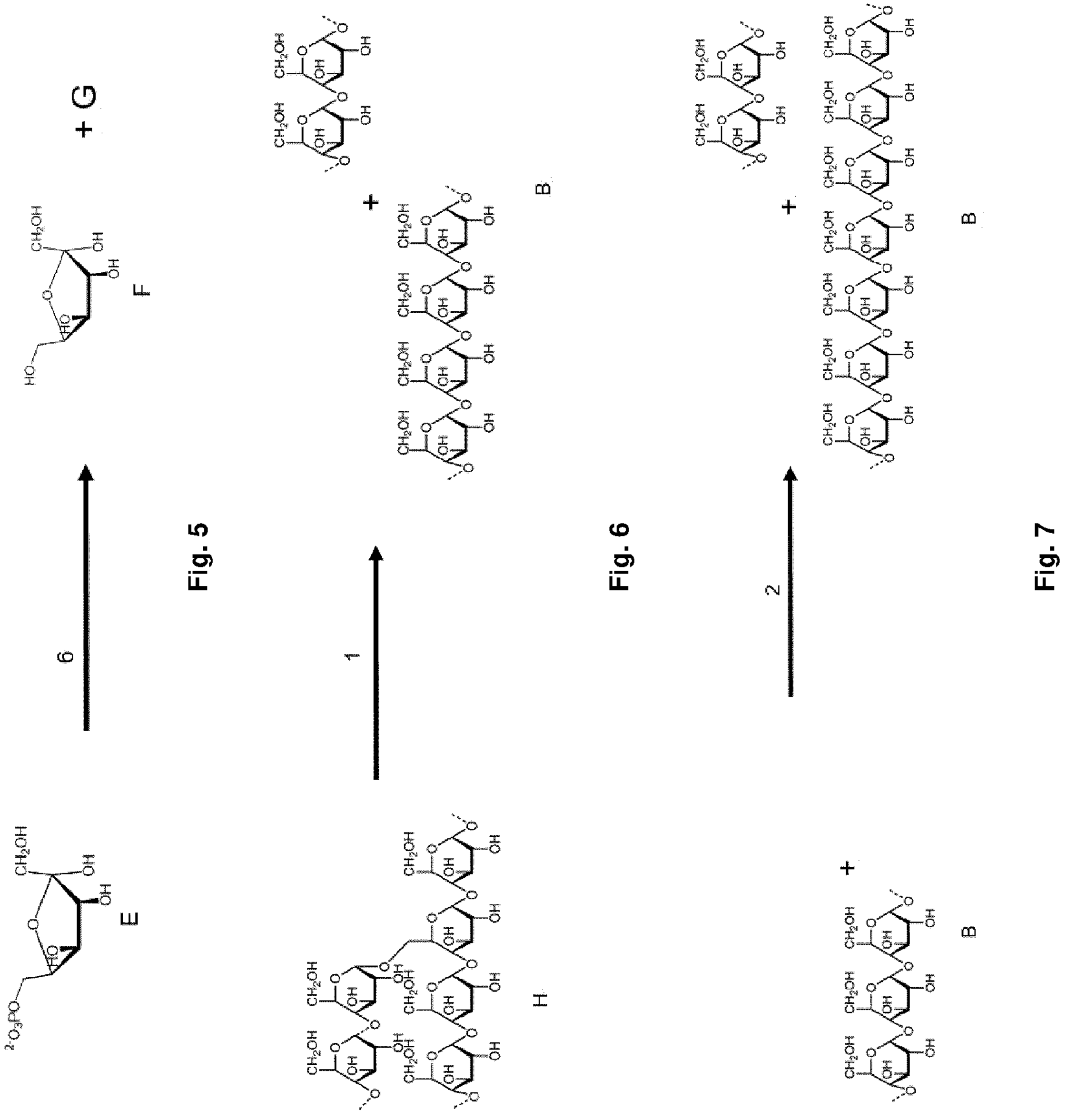
FIG. 5 intermediate step of the process shown in FIG. 1; fructose-6-phosphate is cleaved into fructose (F) and phosphate (G) by the action of a phosphatase (6)
FIG. 6 intermediate step of the process shown in FIG. 1; all α-1,6 linkage contained in starch (A—mixture of amylose (B) and amylopectin (H)) are cleaved by use of a Pullulanase.
FIG. 7 intermediate step of the process shown in FIG. 1; α-Glucanotransferase catalyzes the transfer of a segment of a 1,4- α-D-glucan (B) to a new position in an acceptor carbohydrate (B) generating a new α-1,4 linkage.

FIG. 2 shows an intermediate process step of the general process shown in FIG. 1. Glucan phosphorylase (3) and inorganic phosphate (G) are used to cleave an α-1,4 linkage between the terminal glucose residue and the rest of the polymer (B-A) to release glucose-1-phosphate (C).

FIG. 3 to FIG. 7 show further intermediate steps of the process shown in FIG. 1.

FIGS. 8 to 13 present diagrams of experimental data which are further discussed in the experimental section below.

While the invention has been described with reference to certain preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments, but that the invention will include all embodiments falling within the scope of the appended claims.

Experimental Section

1. Materials

All chemicals were of analytical grade or higher quality and purchased from Sigma-Aldrich, Carbosynth or VWR and used without further purification.

Glucidex 12 and Glucidex 19 are maltodextrin compounds, which were obtained from Roquette Freres (France).

The molecular mass of a glucose polymer can be calculated by using the formula $(180*n-18*(n-1))$ with n the DP (degree of polymerization) of the glucose polymer. The DE (dextrose equivalent) can be calculated as 100*(180/Molecular mass (glucose polymer)). The DP can be calculated using the equation DP=111/DE (Balto, Amy S., et al. "On the use of differential solubility in aqueous ethanol solutions to narrow the DP range of food-grade starch hydrolysis products." Food chemistry 197 (2016): 872-880). Glucidex 12 with a DE between 11-14 an average DP of 8-10 is assumed. Glucidex 19 with a DE between 18-20 an average DP of 5-6 is assumed. But as these preparations are derived by enzymatic treatment there are smaller and larger maltodextrins also included.

The following strains were used during this work: *E. coli* XL1 Blue, *E. coli* BL21(DE3), every construct was successful expressed using autoinduction media at 37° C.

2. Methods

Analytics

Analytics for the complete process as shown in FIG. 1 were performed using a HPLC Dionex Ultimate 3000 system equipped with an autosampler (WPS 3000TRS), a column compartment (TCC3000RS) and a light scattering detector. The YMC Triart Diol Hilic column (100*2 mm, 1.9 μm, 12 nm) at 7° C. was used for separation by gradient elution (15-85%) with 0.1% formic acid pH 4.5, and 0.1% formic acid in ACN as the mobile phase at 0.45 ml $min^{-1}$. Samples were diluted in water/acetonitrile with the ratio of 3:7. Data were analyzed using Dionex Chromeleon software.

Detection of overall ketose (fructose and fructose-6-phosphate) was done using an assay based on triphenyltetrazolium chloride (TTC). The detection method is based on a differential rate of reduction between aldoses and ketoses. Into a 2 ml test tube is added 0.05 ml sample, plus 0.01 ml 1% aqueous TTC, plus 0.04 ml 6 N NaOH. After exactly 5 min, 1.5 ml acetic acid:ethanol (1:9) is added and the test tube contents vortexed. With water used as a blank, absorbance is measured at 480 nm, using a spectrophotometer (Multiskan GO, Thermo Fisher). Glucose and glucose-6-phosphate reduces TTC to a red pigment—a triphenylformazan—about 100 times slower than an equivalent amount of fructose.

Glucose is detected using an assay based on glucose oxidase. 50 μl of the sample or diluted sample is mixed with 50 μl of master mix (0.75 mM ABTS, 2 U/ml glucose oxidase, 0.1 U/ml Peroxidase, 20 mM KPi pH 6.0) and incubated for 30 min at 30° C. and then measured at 418 nm using a spectrophotometer (Multiskan GO, Thermo Fisher).

Protein Expression

Optimized protein expression is exemplarily described for one enzyme and was performed for all proteins by the same procedure.

*E. coli* BL21(DE3) containing the plasmid of interest (pET28 derivative with one gene encoding one of the described enzymes for the process) was grown in 250 ml autoinduction media (Studier, F. William. "Protein production by auto-induction in high-density shaking cultures." Protein expression and purification 41.1 (2005): 207-234). The preculture was incubated in 4 ml of LB medium with 100 μg/ml kanamycin at 37° C. overnight on a rotary shaker (180 rpm). Expression culture was inoculated with a 1:100 dilution of overnight culture. Incubation was performed for 24 h at 37° C. Cells were harvested by centrifugation and resuspended in 50 mM TRIS-HCl (pH 8.0). Crude extracts were prepared by use of a Basic-Z Cell Disrupter (IUL Constant Systems) or an ultrasonic device and subsequent addition of $MgCl_2$ to a final concentration of 2.5 mM in combination with DNaseI (1 μg/ml) and a following incubation for 20 min at room temperature (25° C.) to degrade DNA. Afterwards all crude extracts were heat treated for 30 min at 70° C. The insoluble fraction of the lysate was removed by centrifugation (20,000 rpm for 40 min at 4° C.). The supernatant was filtered through a 0.45 μm syringe filter and used as purified enzyme preparation. Aliquots of each purification were subjected to 12% SDS-Page described by Laemmli Ulrich K. "Cleavage of structural proteins during the assembly of the head of bacteriophage T4." nature 227.5259 (1970): 680).

The enzymes correspond to the following sequences SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49.

Activity Testing of Enzymes

Pullulanase of *Bacillus* flavocaldarius (SEQ ID NO: 1) was tested for activity using pullulan as substrate and 3,5-dinitrosalicylic acid (DNS) for detection.

Pullulanase was incubated with 1% (w/v) pullulan in 50 mM potassium phosphate buffer pH 7.0 and 5 mM $MgCl_2$ at 65° C. At different time points an aliquot of 24 μl was transferred into 96 μl of DNS reagent (10 g 3,5-dinitrosalicylic acid, 300 g sodium potassium tartrate, 16 g sodium hydroxide for 1 liter). Heated up to 95° C. for 5 minutes and afterwards were 100 μl transferred into a flat bottom microtitre plate and measured at 540 nm in a spectrophotometer (Multiskan GO, Thermo Fisher).

α-Glucanotransferase of *Meiothermus ruber* (SEQ ID NO:3) was tested for activity using maltotriose as substrate and the ability to build up larger oligosaccharides. Detection of activity was done using TLC (Isopropanol:Ethylacetate: Water (3:1:1)) and thymol spray reagent (0.5 g thymol, 95 ml ethanol, 5 ml sulfuric acid 97%). α-Glucanotransferase of *Meiothermus ruber* was incubated with 50 mM maltotriose in 50 mM potassium phosphate buffer pH 7.0 and 5 mM $MgCl_2$ at 65° C.

α-Glucan phosphorylase of *Thermotoga naphthophila* (SEQ ID NO: 5) was tested for activity using a combination of enzymes to detect the product α-D-glucose-1-phosphate. α-D-Glucose-1-phosphate was converted to α-D-glucose-6-phosphate which was subsequently oxidized by α-D-glucose-6-phosphate dehydrogenase to α-D-gluconate-6-phosphate. The produced NADH was used to convert WST-1 by using 1-Methoxy-5-methylphenazinium methyl sulfate (PMS) as electron mediator. α-Glucan phosphorylase was incubated with 1% (w/v) soluble starch in 50 mM potassium phosphate buffer pH 7.0 and 5 mM $MgCl_2$ and 0.1 mM Pyridoxal-5-Phosphate at 65° C. At different time points an aliquot of 10 μl was transferred into 190 μl of detection solution containing phosphoglucomutase 0.1 U, α-D-glucose-6-phosphate dehydrogenase 0.1 U, 0.1 mM WST-1, 0.005 mM PMS. The mixture was incubated for 30 min and the measured at 440 nm in a spectrophotometer (Multiskan GO, Thermo Fisher).

Sucrose Phosphorylase of *Bifidobacterium adolescentis* (SEQ ID NO: 51) was tested for activity using sucrose as substrate and 3,5-dinitrosalicylic acid for detection. In an assay using 3,5-dinitrosalicylic acid for detection only the product fructose produces a signal. Sucrose Phosphorylase was incubated with 100 mM sucrose in 100 mM potassium phosphate buffer pH 7.0 and 5 mM $MgCl_2$ at 50° C. At different time points an aliquot of 24 μl was transferred into 96 μl of DNS reagent (10 g 3,5-dinitrosalicylic acid, 300 g sodium potassium tartrate, 16 g sodium hydroxide for 1 liter). Heated up to 95° C. for 5 min and afterwards were 100 μl transferred into a flat bottom microtitre plate and measured at 540 nm in a spectrophotometer (Multiskan GO, Thermo Fisher).

Phosphoglucomutase of Saccharolobus sulfataricus P2 (SEQ ID NO: 7) or Chlostridium *thermocellum* (SEQ ID NO: 9) was tested for activity using α-D-glucose-1-phosphate as substrate and 3,5-dinitrosalicylic acid for detection. In an assay using 3,5-dinitrosalicylic acid for detection only the product α-D-glucose-6-phosphate produces a signal.

Phosphoglucomutase was incubated with 50 mM α-D-glucose-1-phosphate in 50 mM potassium phosphate buffer pH 7.0 and 5 mM $MgCl_2$ at 65° C. At different time points an aliquot of 24 μl was transferred into 96 μl of DNS reagent (10 g 3,5-dinitrosalicylic acid, 300 g sodium potassium tartrate, 16 g sodium hydroxide for 1 liter). Heated up to 95° C. for 5 min and afterwards were 100 μl transferred into a flat bottom microtitre plate and measured at 540 nm in a spectrophotometer (Multiskan GO, Thermo Fisher).

Phosphoglucoisomerase of *Thermotoga maritima* (SEQ ID NO: 11) was tested for activity using fructose-6-phosphate as substrate and α-D-glucose-6-phosphate dehydrogenase for detection. The produced NADH was used to convert WST-1 by using 1-Methoxy methylphenazinium methyl sulfate (PMS) as electron mediator. Phosphoglucoisomerase was incubated with 50 mM fructose-6-phosphate in 50 mM potassium phosphate buffer pH 7.0 and 5 mM $MgCl_2$ at 65° C. At different time points an aliquot of 10 μl was transferred into 190 μl of detection solution containing α-D-glucose-6-phosphate dehydrogenase 0.1 U, 0.1 mM WST-1, 0.005 mM PMS. The mixture was incubated for 30 min and the measured at 440 nm in a spectrophotometer (Multiskan GO, Thermo Fisher).

Phosphatase of *Thermotoga naphthophila* (SEQ ID NOs: 13, 15, 17, 19, 21, 23, 25, 27, 29, 31, 33, 35, 37, 39, 41, 43, 45, 47, 49) was tested for activity using fructose-6-phosphate as substrate and a phosphate assay. The phosphate assay consists of three solutions, solution A (12% (w/v) l-ascorbic acid in 1N HCl solution), solution B (2% (w/v) Na2MoO4×2H2O in ddH2O), solution F (2% (w/v) citric acid and 2% (w/v) acetic acid in ddH2O). Solution D is a 2:1 mixture of solution A and solution B and prepared freshly before the measurement. 75 μl of solution D is pipetted into the needed wells of a flat-bottom microtiter plate. In the next step 25 μl of the sample or a standard with defined concentration is added and incubated for 5 min at room temperature. In the last step the reaction is stopped by addition of 75 μl of solution F and an additional incubation step of 15 min at room temperature. The samples are measured at 655 nm in a spectrophotometer (Multiskan GO, Thermo Fisher).

All tested enzymes fulfill the requirements to catalyze one of the steps within the process and are stable under process conditions (65° C., 50 mM potassium phosphate buffer pH 7.0, 5 mM MgCl2 0.005 mM PLP).

3. Conversion of Starch into Fructose (Inventive Example 1; IE1)

Conversion experiments were performed at a 15 ml scale using 50 ml falcon tubes with 7 grams of native starch. Native starch was pretreated with a volume of 6 ml water and buffer and heated up to 95° C. for 30 min to allow an almost complete swelling. Afterwards, the swollen starch was cooled down to 65° C. and the enzymes were added. To 7 grams of native starch a volume of 10.5 ml of buffer, salts and enzymes was added. Additionally, maltose was added to a final concentration of 10 mM. The final mixture contained 50 mM KPi pH 7.0, 5 mM $MgCl_2$, 0.1 mM PLP, 10 mM Maltose, 0.4 mg Pullulanase, 1.5 mg α-Glucanotransferase, 30 mg α-Glucan phosphorylase, 1.4 mg Phosphoglucomutase. 1.2 mg Phosphoglucoisomerase and 14 mg Phosphatase. Enzymes from *Bacillus* flavocaldarius, *Meiothermus ruber, Thermotoga naphthophila* (phosphorylase and phosphatase), Chlostridium *thermocellum* and *Thermotoga maritima* were used. Starting with 0 hours' incubation on a regular basis samples were taken and filtered using a 10 kDa spin filter (VWR 82031-350). If necessary, samples were diluted in water/acetonitrile with the ratio of 3:7 for further analytics.

Figure 8:
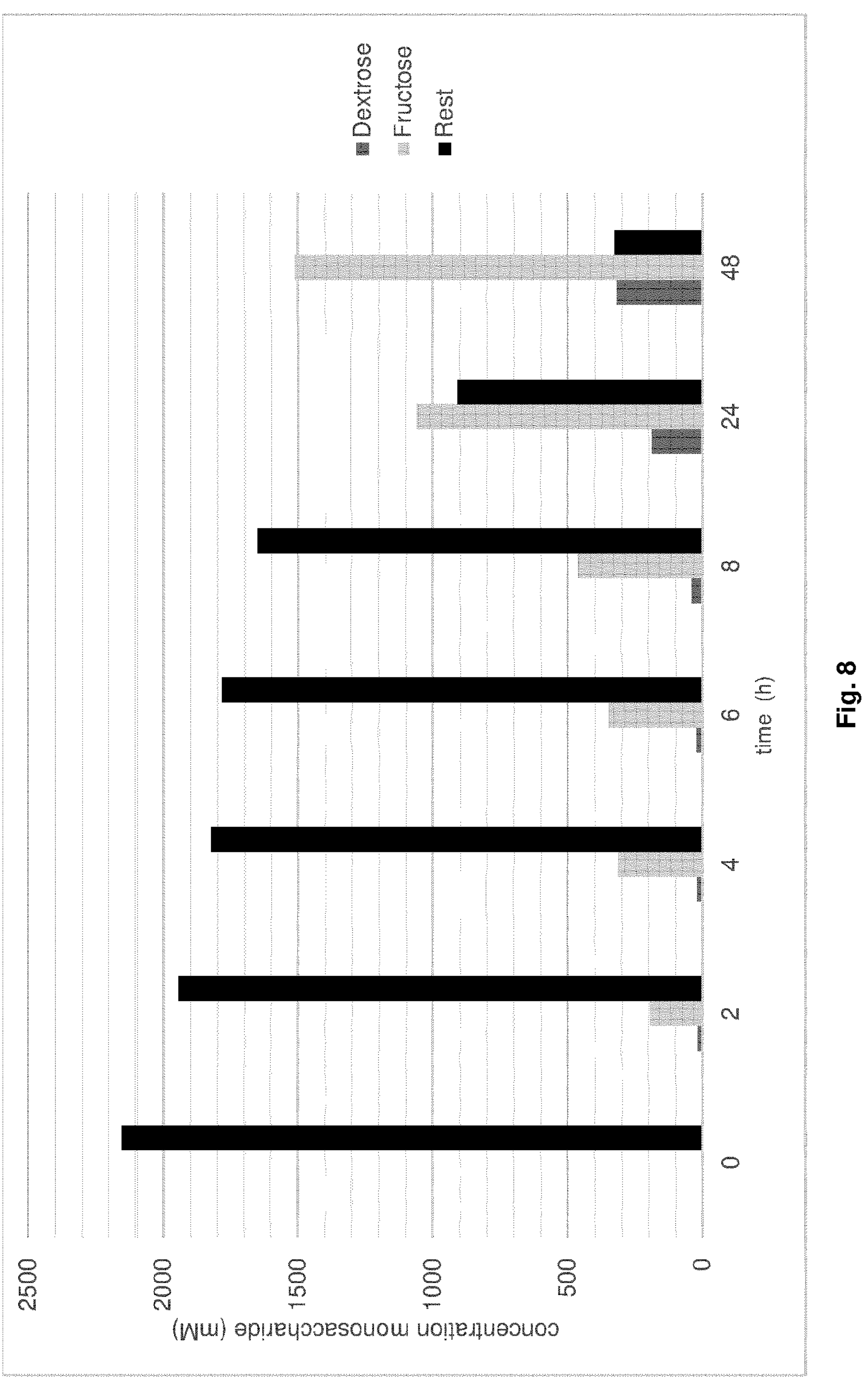
FIG. 8 diagram showing the progress of the optimized process using an improved phosphatase, namely P46T, and maltose (0.1 mM) for faster conversion of native starch within 48 hours.

The results of the conversion of starch into fructose according to Inventive Example 1 (IE1) (35% dry substance starch correspond to 2153.5 mM concentration of monosaccharides) are shown in Table 1 as well as in FIG. 8.

TABLE 1

| | Inventive Example 1 | | |
|---|---|---|---|
| Time [h] | Fructose [mM] | Dextrose [mM] | Rest [mM] |
| 0 | 0 | 0 | 2153.5 |
| 2 | 194 | 16 | 1943.5 |
| 4 | 312 | 18 | 1823.5 |
| 6 | 349 | 22 | 1782.5 |
| 8 | 464 | 40 | 1649.5 |
| 24 | 1059 | 186 | 908.5 |
| 48 | 1511 | 317 | 325.5 |

From Table 1 can be derived that after 48 h fructose in a yield of about 70% is obtained.

4. Conversion of Starch to Fructose in the Presence of Maltose (IE2-IE5), Maltotriose (IE6-IE9), Maltotetraose (IE10-IE12), Maltodextrin Glucidex 12 (IE13-IE15) or Maltodextrin Glucidex 19 (IE16-IE18)

Potassium phosphate buffer 50 mM pH 7.0, $MgCl_2$ 5 mM, PLP 0.005 mM, swollen native starch 1% (w/v), Maltose (0.01 mM, 0.1 mM, 1.0 mM or 10 mM; IE2-IE5) or Maltotriose (0.01 mM, 0.1 mM, 1.0 mM or 10 mM; IE6-IE9) or Maltrotetraose (0.01 mM, 0.1 mM or 1.0 mM; IE10-IE12) or Maltodextrin Glucidex 12 (0.0342% (w/v), 0.00342% (w/v) or 0.000342% (w/v); IE13-IE15) or Maltodextrin Glucidex 19 (0.0342% (w/v), 0.00342% (w/v) or 0.000342% (w/v); IE16-IE18), glucan phosphorylase (0.0025 mg/ml), alpha-glucanotransferase (0.075 mg/ml), pullulanase (0.02 mg/ml) in a total volume of 5 ml was incubated at 65° C. for one hour and aliquots were removed to check for glucose-1-phosphate. The glucose-1-phosphate assay is described under activity testing of enzymes above.

Comparative Examples 1 to 5 (CE1-CE5) were performed by just adding 1 mM of Maltose, Maltotriose, Maltotetraose, Glucidex 12 or Glucidex 19, respectively, without the addition of starch. Comparative Example 6 was performed without the addition of an additional saccharide such as maltose, maltotriose, maltotetraose, Glucidex 12 or Glucidex 19.

Figure 9:
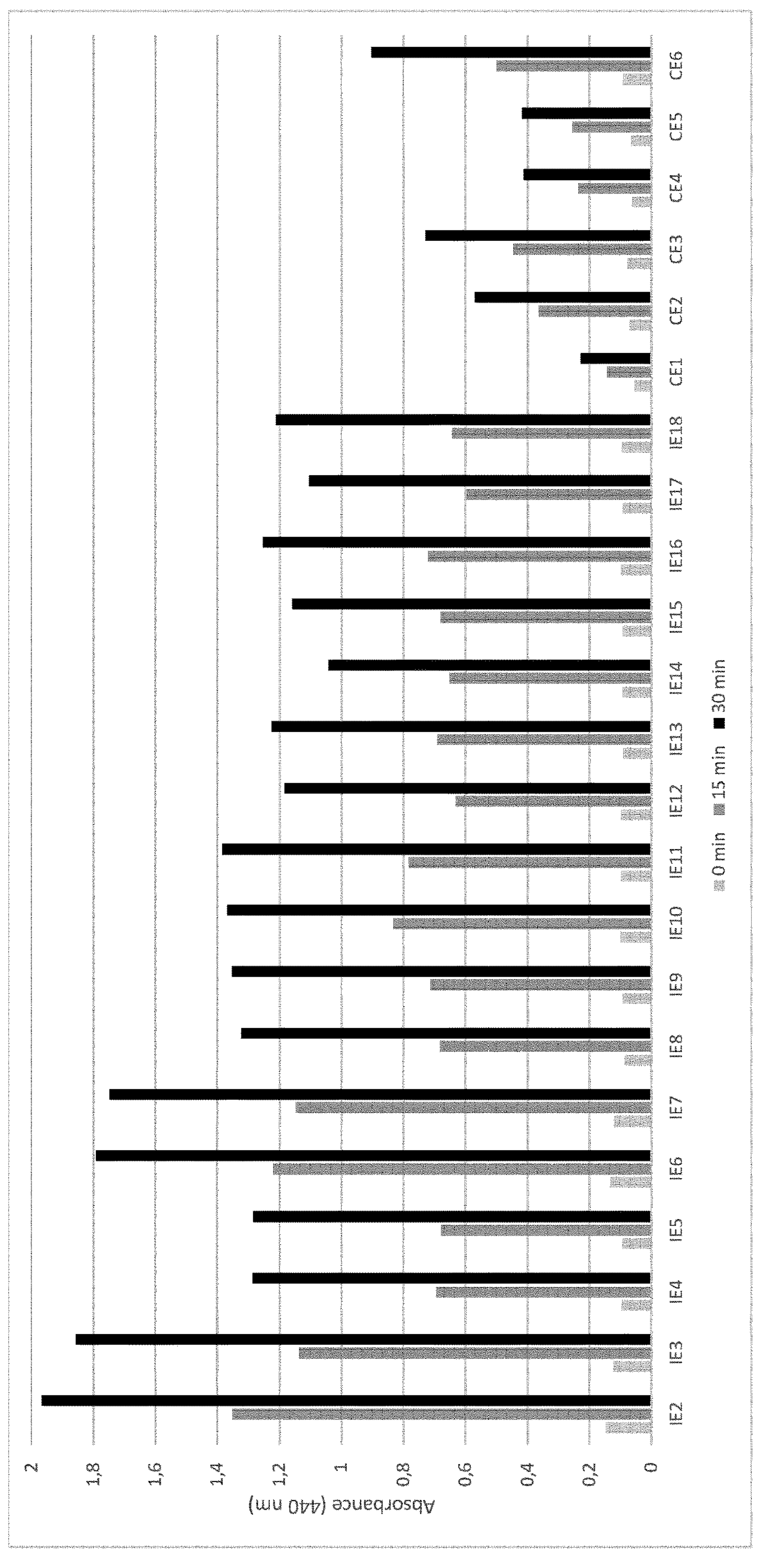
FIG. 9 diagram showing the results of an experimental setting proofing the beneficial impact of short oligosaccharides for the breakdown of native starch using Pullulanase, α-Glucanotransferase and glucan phosphorylase and detection of the produced G1P.

The results of the test on the influence of additional saccharides, such as short oligosaccharides like Maltose, Maltotriose, Maltotetraose, Glucidex 12 or Glucidex 19 on the conversion rate to glucose-1-phosphate is shown in Table 2. The respective diagram is shown in FIG. 9.

TABLE 2

| | Absorbance at 440 nm | | |
|---|---|---|---|
| Example (saccharide residue) | at 0 [min] | at 15 [min] | at 30 [min] |
| IE 2 (Maltose 10 mM) | 0.147 | 1.351 | 1.966 |
| IE 3 (Maltose 1 mM) | 0.125 | 1.138 | 1.857 |
| IE 4 (Maltose 0.1 mM) | 0.096 | 0.694 | 1.288 |
| IE 5 (Maltose 0.01 mM) | 0.095 | 0.678 | 1.286 |
| IE 6 (Maltotriose 10 mM) | 0.134 | 1.222 | 1.793 |
| IE 7 (Maltotriose 1 mM) | 0.120 | 1.148 | 1.748 |
| IE 8 (Maltotriose 0.1 mM) | 0.087 | 0.681 | 1.323 |
| IE 9 (Maltotriose 0.01 mM) | 0.094 | 0.713 | 1.352 |
| IE 10 (Maltotetraose 1 mM) | 0.101 | 0.832 | 1.369 |
| IE 11 (Maltotetraose 0.1 mM) | 0.097 | 0.784 | 1.383 |
| IE 12 (Maltotetraose 0.01 mM) | 0.097 | 0.629 | 1.184 |
| IE 13 (Glucidex 12 0.0342% (w/v)) | 0.092 | 0.689 | 1.226 |
| IE 14 (Glucidex 12 0.00342% (w/v)) | 0.093 | 0.652 | 1.042 |
| IE 15 (Glucidex 12 0.000342% (w/v)) | 0.094 | 0.679 | 1.159 |
| IE 16 (Glucidex 19 0.0342% (w/v)) | 0.099 | 0.720 | 1.254 |
| IE 17 (Glucidex 19 0.00342% (w/v)) | 0.093 | 0.595 | 1.106 |
| IE 18 (Glucidex 19 0.000342% (w/v)) | 0.095 | 0.643 | 1.212 |
| CE 1 (only Maltose (1 mM)) | 0.053 | 0.144 | 0.228 |
| CE 2 (only Maltotriose (1 mM)) | 0.068 | 0.364 | 0.569 |
| CE 3 (only Maltotetraose (1 mM)) | 0.079 | 0.446 | 0.728 |
| CE 4 (only Glucidex 12 0.0342% (w/v)) | 0.063 | 0.237 | 0.413 |
| CE 5 (only Glucidex 19 0.0342% (w/v)) | 0.065 | 0.255 | 0.418 |
| CE 6 (native starch) | 0.092 | 0.500 | 0.905 |

Conversion of large polysaccharides such as starch or comparable substrates like cellulose, and the like, within the process contains one major rate-limiting step, the generation of glucose-1-phosphate molecules catalyzed for example by a glucan phosphorylase. The phosphorylase needs accessible ends of the polysaccharide to catalyze cleavage of an α-1,4 linkage using inorganic phosphate between the terminal glucose residue and the rest of the polymer to release glucose-1-phosphate. The combined action of pullulanase, α-Glucanotransferase and short oligosaccharides such as maltose (IE2-IE5), maltotriose (IE6-IE9), maltotetraose (IE10-IE12), Maltodextrin Glucidex 12 (IE13-IE15) or Maltodextrin Glucidex 19 (IE16-IE18), cf. Table 2, show that the conversion rate is increased by the addition of short oligosaccharides.

This leads to a higher glucose-1-phosphate production and therefore allows a faster conversion of starch into fructose within the inventive process.

The conversion rate for all Comparative Examples 1 to 6 is lower in comparison to the Inventive Examples 2 to 18.

5. Phosphate Assays

For monitoring the different activities of the different phosphatases and the variants for two sugar-phosphate intermediates occurring in the process a phosphate assay was performed.

The reaction mixture contained 50 mM TRIS-HCl buffer pH 7.0, 2.5 mM $MgCl_2$, 10 mM of G1 P, G6P or F6P and one phosphatase (0.003 mg/ml) in a total volume of 1 ml. The mixture was incubated at 65° C. and in regular time intervals an aliquot was removed and tested for released phosphate. The phosphate assay is described above in further detail.

Figure 10:
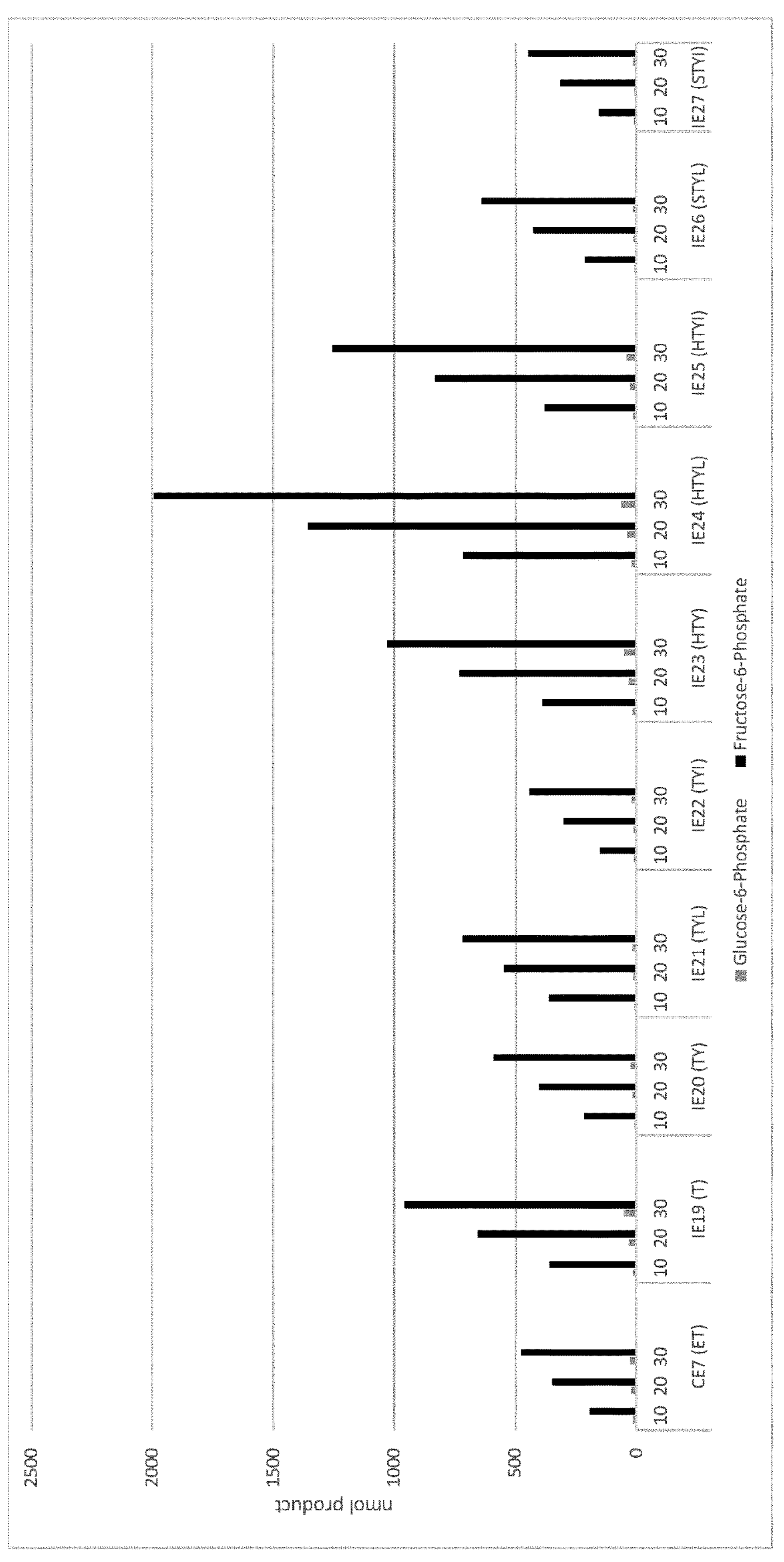
FIG. 10 diagram showing the comparison between wild-type phosphatase and nine variants (P46T, P46TE47Y, P46TE47YG50L, Y23HP46TE47Y, P46TE47YG50I, Y23HP46TE47YG50L, Y23HP46TE47YG50I, Y23SP46TE47YG50L, Y23SP46TE47YG50I) for their improved catalytic performance in context of the three different sugar-phosphates (G6P and F6P) occurring in the process.

The results of the phosphate assay are shown in Table 3 and FIG. 10. The amount of G6P and F6P were detected and the ratio of F6P/G6P was determined. The ratio of F6P/G6P refers to the selectivity of the tested phosphatases.

TABLE 3

| | | Released Phosphate | | |
|---|---|---|---|---|
| Example (Phosphatase) | Time [min] | G6P [nmol] | F6P [nmol] | F6P/G6P ratio |
| CE7 (WT) | 10 | 12.165 | 194.647 | 16 |
| | 20 | 20.276 | 347.584 | 17.143 |
| | 30 | 25.490 | 476.191 | 18.682 |
| IE19 (T) | 10 | 12.745 | 358.591 | 28.136 |
| | 20 | 31.862 | 652.879 | 20.491 |
| | 30 | 50.400 | 958.753 | 19.023 |
| IE20 (TY) | 10 | 6.952 | 216.082 | 31.083 |
| | 20 | 15.641 | 400.301 | 25.593 |
| | 30 | 23.752 | 590.314 | 24.854 |
| IE21 (TYL) | 10 | 5.793 | 363.226 | 62.700 |
| | 20 | 11.296 | 547.735 | 48.487 |
| | 30 | 15.062 | 717.182 | 47.615 |
| IE22 (TYI) | 10 | 8.110 | 151.199 | 18.643 |
| | 20 | 9.848 | 300.660 | 30.529 |
| | 30 | 17.959 | 442.011 | 24.613 |
| IE23 (HTY) | 10 | 15.641 | 387.557 | 24.778 |
| | 20 | 31.862 | 729.348 | 22.891 |
| | 30 | 48.082 | 1027.691 | 21.373 |
| IE24 (HTYL) | 10 | 17.959 | 714.865 | 39.806 |
| | 20 | 37.945 | 1357.896 | 35.786 |
| | 30 | 62.565 | 1993.975 | 31.870 |
| IE25 (HTYI) | 10 | 12.745 | 379.446 | 29.773 |
| | 20 | 25.490 | 832.464 | 32.659 |
| | 30 | 39.393 | 1256.517 | 31.897 |
| IE26 (STYL) | 10 | 5.214 | 213.185 | 40.889 |
| | 20 | 9.848 | 426.949 | 43.353 |
| | 30 | 13.324 | 637.238 | 47.826 |
| IE27 (STYI) | 10 | 7.531 | 155.834 | 20.692 |
| | 20 | 6.372 | 313.405 | 49.182 |
| | 30 | 13.324 | 448.963 | 33.696 |

The introduction of the mutation P46T (IE19 (T)) into the phosphatase of *Thermotoga naphthophila* increases overall activity of the enzyme and reduces the activity of the enzyme towards glucose-6-phosphate (G6P) as can be derived from Table 3 as well as FIG. 10. This allows better process economics in context of reduced enzyme amounts and a better overall fructose production. P46TE47Y (IE20 (TY)) has a slightly improved activity for F6P compared to the wildtype (CE7 (WT)) and much around the same activity towards G6P reducing unwanted side products like glucose. P46TE47YG50L (IE21 (TYL)) has an improved activity for F6P compared to the wildtype (CE7 (WT)) and a reduced activity towards G6Palso reducing unwanted side products like glucose. Y23HP46TE47Y (IE23 (HTY)) also has an improved activity for F6P compared to CE7 (WT) and a slightly increased activity towards G6P. But in relation to both activities this variant shows also an improved performance for the inventive process allowing an improved process reducing unwanted side products like glucose. P46TE47YG50I (IE22 (TYI)) has an improved selectivity towards F6P. Y23HP46TE47YG50L (IE24 (HTYL)) has an improved activity for F6P compared to CE7 (WT) and a reduced activity towards G6P in context of an overall increased activity. Y23HP46TE47YG50I (IE25 (HTYI)) has an improved activity for F6P and a reduced activity towards G6 Pin context of an overall increased activity. Y23SP46TE47YG50L (IE26 (STYL)) has an improved activity for F6P compared to CE7 (WT) and a reduced activity towards G6 Pin context of an overall increased activity. Y23SP46TE47YG50I (IE27 (STYI)) has an improved selectivity towards F6P.

The inventive phosphatases, cf. Table 3 and FIG. 10, show increased activity, increased selectivity or both.

Figure 11:
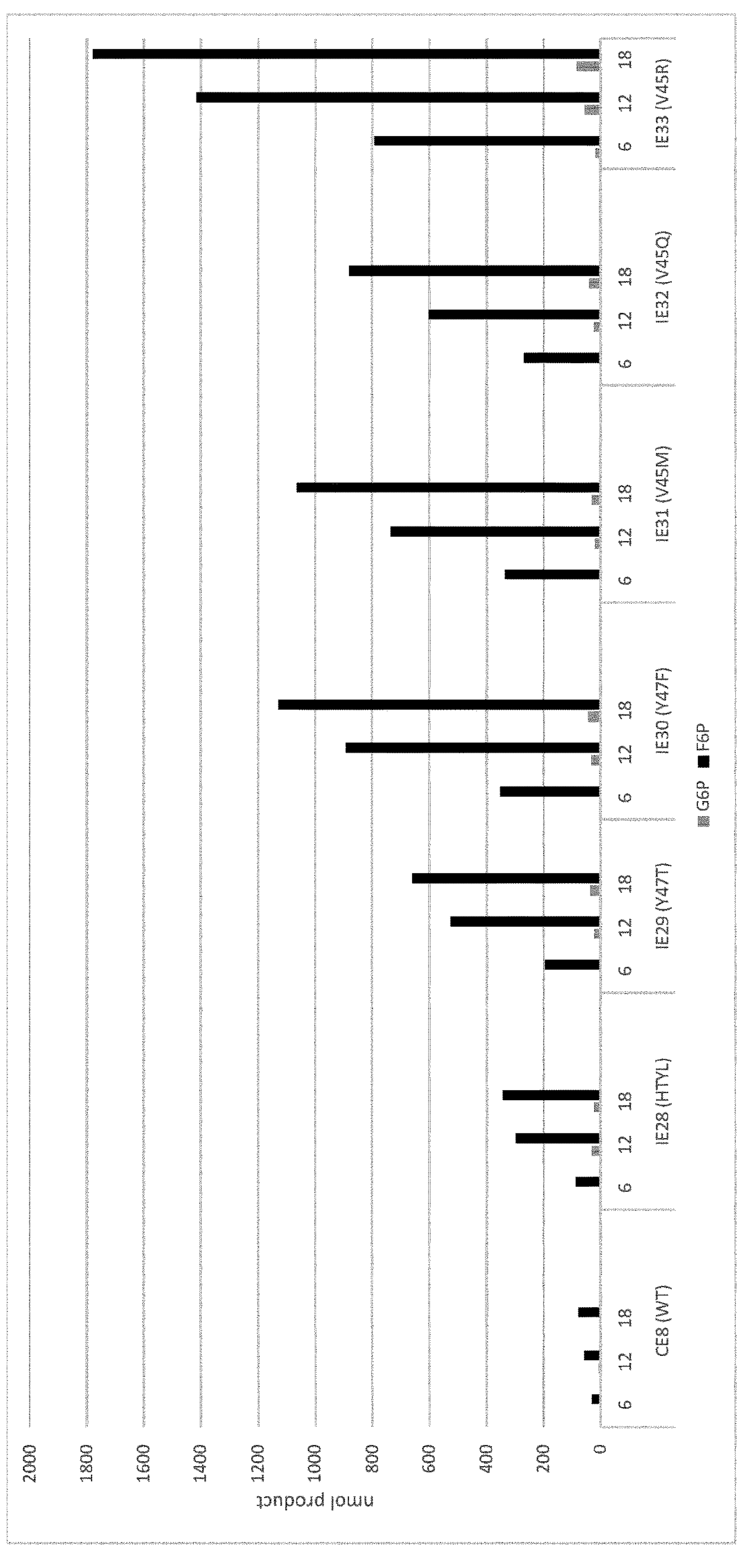
FIG. 11 diagram showing the comparison between wild-type phosphatase and six variants (HTYL, Y47T, Y47F, V45M, V45Q and V45R) for their improved catalytic performance in context of the three different sugar-phosphates (G6P and F6P) occurring in the process.

The results of a further phosphate assay testing additional phosphatases in comparison to a wild-type phosphatase are shown in Table 4 and FIG. 11. As the phosphatases used showed an improved activity the time intervals taken for measurements were shortened.

TABLE 4

| | | Released Phosphate | | |
|---|---|---|---|---|
| Example (Phosphatase) | Time [min] | G6P [nmol] | F6P [nmol] | F6P/G6P ratio |
| CE8 (WT) | 6 | 1.30 | 30.34 | 23.33 |
| | 12 | 5.75 | 58.71 | 10.19 |
| | 18 | 4.36 | 76.96 | 17.63 |
| IE28 (HTYL) | 6 | 1.08 | 86.67 | 80.05 |
| | 12 | 31.15 | 298.15 | 9.57 |
| | 18 | 22.02 | 341.79 | 15.51 |
| IE29 (Y47T) | 6 | 1.29 | 194.18 | 149.64 |
| | 12 | 22.42 | 526.27 | 23.46 |
| | 18 | 37.10 | 659.17 | 17.76 |
| IE30 (Y47F) | 6 | 2.27 | 354.07 | 155.77 |
| | 12 | 31.94 | 893.24 | 27.96 |
| | 18 | 43.05 | 1129.69 | 26.23 |
| IE31 (V45M) | 6 | 1.97 | 335.33 | 170.03 |
| | 12 | 17.76 | 735.26 | 41.38 |
| | 18 | 30.47 | 1064.51 | 34.92 |
| IE32 (V45Q) | 6 | 1.97 | 267.81 | 135.80 |
| | 12 | 23.72 | 602.21 | 25.38 |
| | 18 | 40.80 | 881.02 | 21.59 |
| IE33 (V45R) | 6 | 17.46 | 792.46 | 45.38 |
| | 12 | 55.09 | 1415.99 | 25.69 |
| | 18 | 83.29 | 1778.20 | 21.34 |

Y23HP46TE47YG50L (HTYL) has an improved activity for F6P compared to the wildtype and a reduced activity towards G6P in context of an overall increased activity. For this reason, the enzyme allows an improved process reducing unwanted side products like glucose. The same applies to variants Y23HP46TE47TG50L (Y47T) Y23HP46TE47TG50L (Y47F), Y23HV45MP46TE47TG50L (V45M), Y23HV45QP46TE47TG50L (V450), Y23HV45RP46TE47TG50L (V45R).

Figure 12:
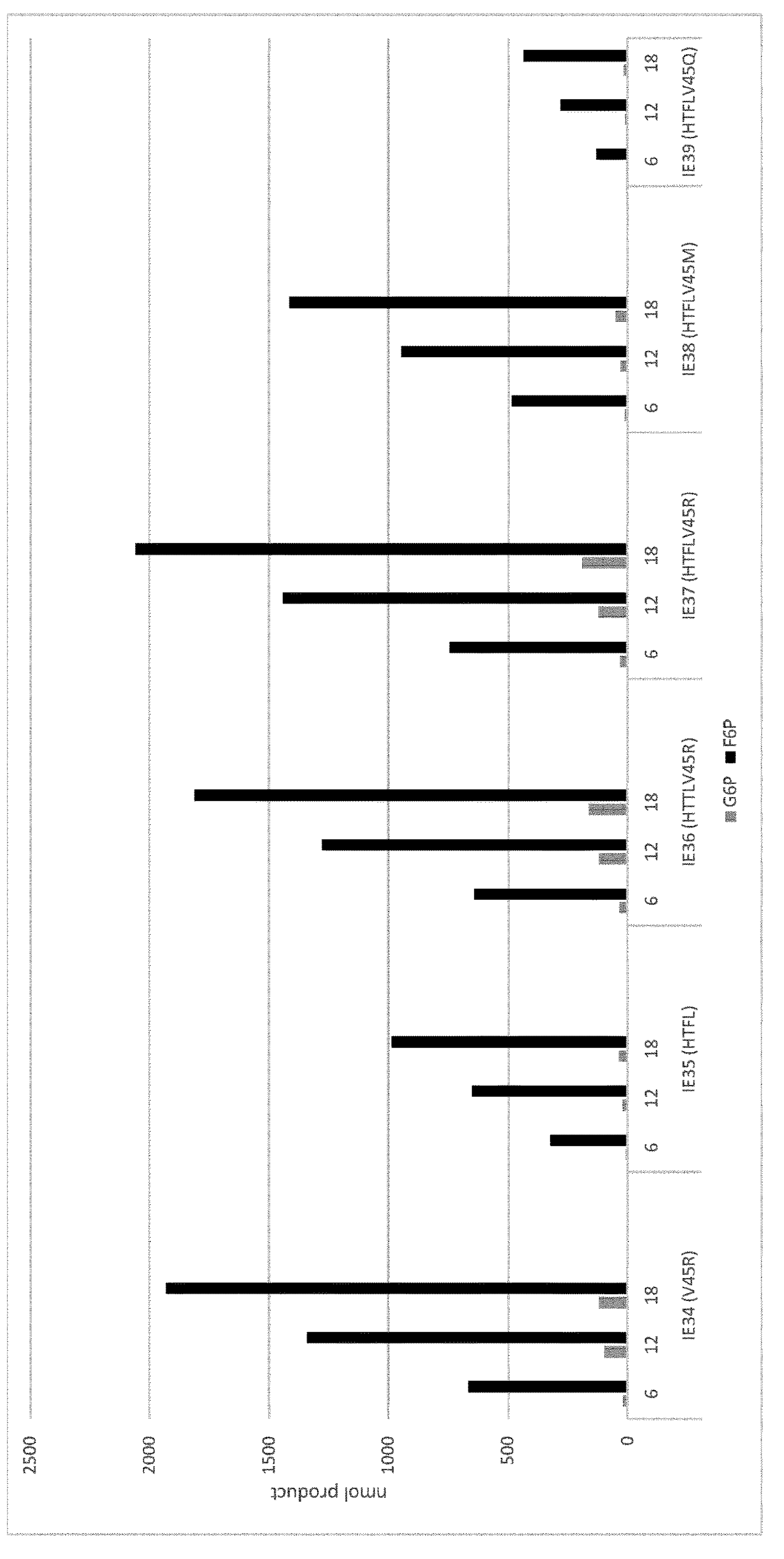
FIG. 12 diagram showing the comparison between six phosphatase variants (V45R, HTFL, HTTLV45R, HTFLV45R, HTFLV45M and HTFLV45Q) for their improved catalytic performance in context of the three different sugar-phosphates (G6P and F6P) occurring in the process.

The results of another phosphate assay testing additional phosphatases are shown in Table 5 and FIG. 12. As the phosphatases used showed an improved activity the time intervals taken for measurements were also shortened.

TABLE 5

| Example (Phosphatase) | Time [min] | Released Phosphate G6P [nmol] | F6P [nmol] | F6P/G6P ratio |
|---|---|---|---|---|
| IE34 (V45R) | 6 | 19.71 | 666.26 | 33.79 |
| | 12 | 95.16 | 1339.62 | 14.07 |
| | 18 | 119.81 | 1928.61 | 16.09 |
| IE35 (HTFL) | 6 | 6.58 | 324.47 | 49.27 |
| | 12 | 21.98 | 648.58 | 29.49 |
| | 18 | 36.96 | 985.68 | 26.66 |
| IE36 (HTTLV45R) | 6 | 33.29 | 639.46 | 19.20 |
| | 12 | 119.11 | 1278.51 | 10.73 |
| | 18 | 161.27 | 1811.74 | 11.23 |
| IE37 (HTFLV45R) | 6 | 32.58 | 743.82 | 22.82 |
| | 12 | 120.89 | 1441.85 | 11.92 |
| | 18 | 190.58 | 2056.57 | 10.79 |
| IE38 (HTFLV45M) | 6 | 10.78 | 483.30 | 44.82 |
| | 12 | 28.63 | 945.95 | 33.03 |
| | 18 | 49.90 | 1414.95 | 28.35 |
| IE39 (HTFLV45Q) | 6 | 1.68 | 129.95 | 77.05 |
| | 12 | 9.04 | 281.23 | 31.09 |
| | 18 | 13.87 | 436.05 | 31.43 |

Variants Y23HV45RP46TE47TG50L (V45R), Y23HP46TE47FG50L (HTFL), Y23HV45RP46TE47TG50L (HTTLV45R), Y23HV45MP46TE47FG50L (V45M) and Y23HV45QP46TE47FG50L (V45Q) all have an improved activity for F6P and a reduced activity towards G6P in context of an overall increased activity. For this reason, the enzymes allows an improved process reducing unwanted side products like glucose.

6. Conversion of Sucrose to Fructose Using Improved Phosphatase Enzymes

Potassium phosphate buffer 50 mM pH 7.0, $MgCl_2$ 5 mM, sucrose 1000 mM, sucrose phosphorylase (0.25 mg/ml), Phosphoglucomutase. (0.04 mg/ml), Phosphoglucoisomerase (0.075 mg/ml) and Phosphatase (0.18 mg/ml) in a total volume of 10 ml were incubated at 50° C. for 48 hours and aliquots were removed to check for glucose and fructose concentration. Enzymes from *Bifidobacterium adolescentis* (sucrose phosphorylase), *Thermotoga naphthophila* (phosphatase), Chlostridium *thermocellum* (phosphoglucomutase) and *Thermotoga maritima* (phosphoglucoisomeraese) were used. Fructose was determined as described in the methods.

Figure 13:
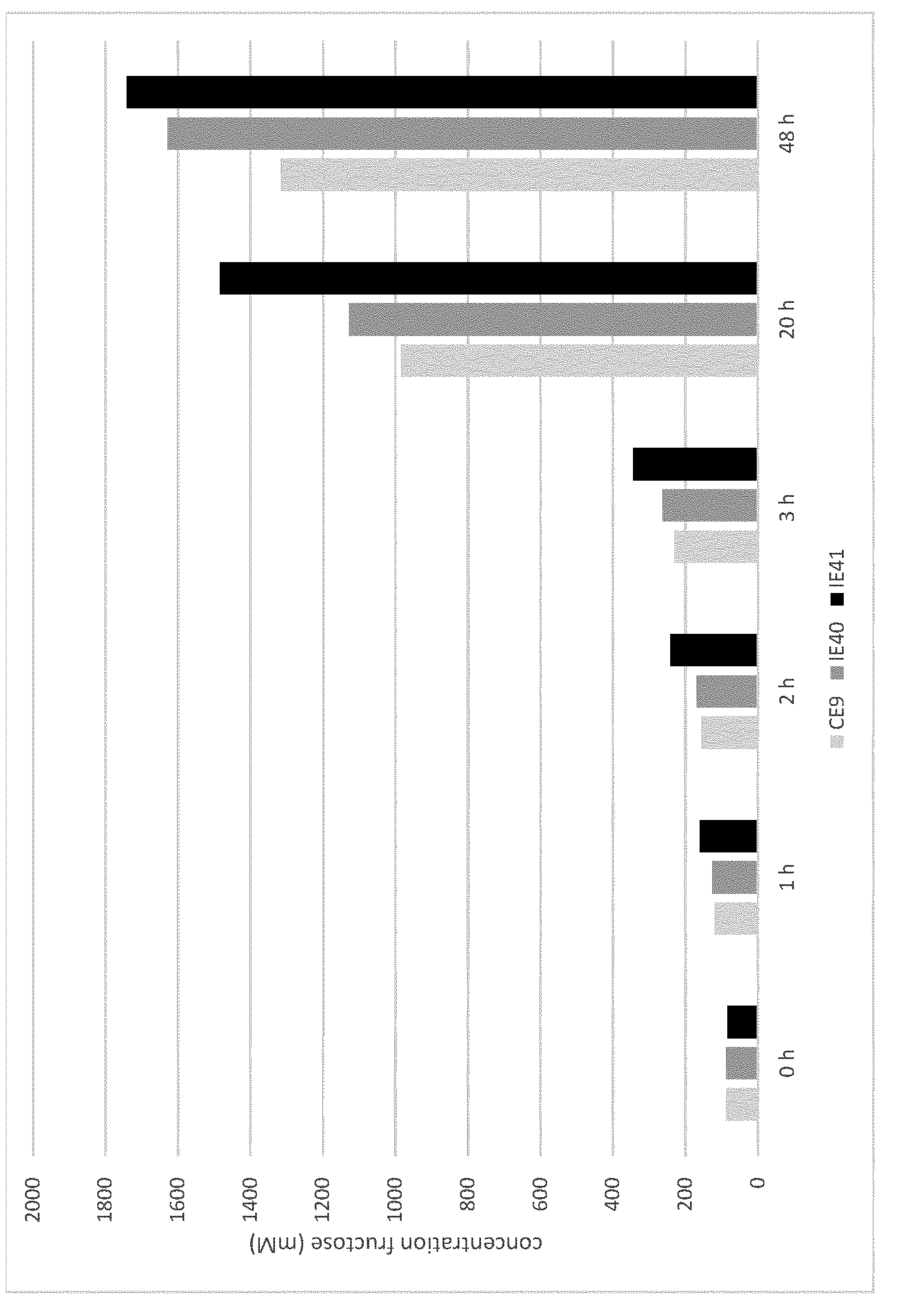
FIG. 13 diagram showing the comparison between wild-type phosphatase and two variants (TY and HTYL) for their improved catalytic performance in context of the conversion of sucrose to fructose.

In Table 6 and FIG. 13 the results of the conversion of sucrose to fructose using three different phosphatase enzymes is shown.

TABLE 6

| Time [h] | Fructose concentration [mM] CE9 (WT) | IE40 (TY) | IE41 (HTYL) |
|---|---|---|---|
| 0 | 88.325 | 88.325 | 85.077 |
| 1 | 119.436 | 126.615 | 160.462 |
| 2 | 157.385 | 169.692 | 241.145 |
| 3 | 230.034 | 262.855 | 344.393 |
| 20 | 984.103 | 1127.692 | 1484.957 |
| 48 | 1317.436 | 1628.547 | 1741.368 |

As can be derived from Table 6 the conversion rates of the inventive phosphatases TY (IE40) and HTYL (IE41) are higher compared to the wild-type phosphatase WT (CE9).

The invention claimed is:

1. A method for converting at least one oligosaccharide and/or polysaccharide into fructose comprising the steps of:

a) adding to a composition comprising water, phosphate, at least one oligosaccharide and/or polysaccharide, at least six enzymes, and b) subsequently enzymatically converting the at least one oligosaccharide and/or polysaccharide to fructose in the presence of the at least six enzymes, wherein in step a) at least one additional saccharide is added, whereby the at least one additional saccharide is selected from the group consisting of tetradecasaccharides, tridecasaccharides, dodecasaccharides, undecasaccharides, decasaccharides, nonasaccharides, octasaccharides, heptasaccharides, hexasaccharides, pentasaccharides, tetrasaccharides, trisaccharides, and/or disaccharides;

wherein in step a) the at least six enzymes that are added to the composition include at least one transferase, at least one phosphorylase, at least one mutase, at least one isomerase, and at least one hydrolase;

wherein at least one enzyme of the at least six enzymes in step a) is a phosphatase;

wherein the at least one oligosaccharide and/or polysaccharide is selected from glucose-based oligosaccharide and/or polysaccharides; and wherein the phosphatase comprises an amino acid sequence that is at least 99% identical with the sequence according to SEQ ID NO: 41.

2. The method according to claim 1, wherein the composition in step a) comprises equal or less than 35% of the at least one oligo- and/or polysaccharide on a dry weight basis; and/or wherein the at least one oligosaccharide and/or polysaccharide is selected from the group consisting of starch and derivatives thereof, hemicellulose and derivatives thereof, cellulose and derivatives thereof and/or combinations thereof.

3. The method according to claim 1, wherein in step b) the enzymatic conversion is a one-pot reaction.

4. The method according to claim 1, wherein in step a) the at least one transferase is, a glycosyltransferase; and/or wherein in step a) the at least one phosphorylase is a glucanphosphorylase; and/or wherein in step a) the at least one mutase is a phosphoglucomutase; and/or wherein in step a) the at least one isomerase is a phosphoglucoisomerase; and/or wherein in step a) the at least one hydrolase is a glucanohydrolase.

5. The method according to claim 1, wherein step b) is performed for at least 24 hours at room temperature.

6. The method according to claim 1, wherein at least 50% of the saccharides present in the composition of step a) are converted to fructose after 24 hours of enzymatic conversion; and/or wherein at least 70% of the saccharides present in the composition of step a) are converted to fructose after 48 hours of enzymatic conversion.

7. The method according to claim 1, wherein the temperature in step b) is between 10-100° C.; and/or wherein the pH of the composition is between 3 to 12.

8. The method of claim 1, wherein in step a) the at least one additional saccharide is selected from maltose, maltotriose, and/or maltotetraose.

9. The method of claim 1, wherein in step b) saccharide phosphates are intermediates produced.

10. The method of claim 1, wherein the temperature in step b) is between 20-90° C.; and/or wherein the pH of the composition is between 4 to 10.

* * * * *